(12) United States Patent
Wehner et al.

(10) Patent No.: US 6,399,620 B1
(45) Date of Patent: Jun. 4, 2002

(54) CYCLOALKYL DERIVATIVES AS INHIBITORS OF BONE RESORPTION AND VITRONECTIN RECEPTOR ANTAGONISTS

(75) Inventors: Volkmar Wehner, Sandberg; Jochen Knolle, Kriftel; Hans Ulrich Stilz, Frankfurt, all of (DE); Jean-Francois Gourvest, Biberonne; Denis Carniato, Clamart, both of (FR); Thomas Richard Gadek, Oakland, CA (US); Robert McDowell, San Francisco, CA (US); Robert Maurice Pitti, El Cerrito, CA (US); Sarah Catherine Bodary, San Bruno, CA (US)

(73) Assignee: Aventis Pharma S.A., Frankfurt (DE)

( * ) Notice: Subject to any disclaimer, the term of this patent is extended or adjusted under 35 U.S.C. 154(b) by 0 days.

(21) Appl. No.: 09/606,080

(22) Filed: Jun. 29, 2000

Related U.S. Application Data

(63) Continuation of application No. 08/899,503, filed on Jul. 24, 1997, now abandoned.

(30) Foreign Application Priority Data

Jul. 24, 1996 (DE) .......................... 196 29 816

(51) Int. Cl.$^7$ ...................... A61K 31/505; A61K 31/53; A61P 19/08; A61P 35/00; C07D 239/02

(52) U.S. Cl. .................. 514/256; 514/86; 514/183; 514/241; 514/242; 514/245; 514/269; 514/272; 514/274; 514/275; 544/179; 544/182; 544/198; 544/209; 544/212; 544/215; 544/216; 544/217; 544/218; 544/219; 544/238; 544/243; 544/294; 544/295; 544/296; 544/297; 544/310; 544/312; 544/315; 544/316; 544/318; 544/321; 544/330; 544/331; 544/332; 544/319; 544/333; 544/335

(58) Field of Search .................. 514/256, 269, 514/272, 274, 275; 544/294, 297, 310, 312, 315, 316, 318, 319, 321, 330, 331, 332, 333, 335

(56) References Cited

U.S. PATENT DOCUMENTS

| 5,397,796 A | 3/1995 | Zoller et al. ............... 514/389 |
| 5,981,492 A | 11/1999 | Zoller et al. ............... 514/20 |
| 6,017,925 A | 1/2000 | Duggan ....................... 514/300 |

FOREIGN PATENT DOCUMENTS

| AU | B-34988/93 | 5/1993 |
| EP | 0 518 586 | 12/1992 |
| EP | 0 528 586 | 2/1993 |
| EP | 0 528 587 | 2/1993 |
| EP | 0 566 919 A1 | 10/1993 |
| EP | 97112198 | 3/2000 |
| WO | WO 93/18057 | 9/1993 |
| WO | WO 94/08577 | 4/1994 |
| WO | WO 94/12181 | 6/1994 |
| WO | WO 95/14008 | 5/1995 |
| WO | WO 95/32710 | 12/1995 |
| WO | WO 96/00574 | 1/1996 |
| WO | WO 96/00730 | 1/1996 |
| WO | 97/23451 | 7/1997 |
| WO | WO 98/31359 | 7/1998 |

OTHER PUBLICATIONS

Friedlander, et al., "Definition of Two Angiogenic Pathways by Distince $\alpha_v$ Integins", *Science*, vol. 270:1500–02 (Dec. 1955).

Brown, et al., "Stimulation of migration of human aortic smooth muscle cells by vitro–nectin: implications for atherosclerosis", *Cardiovascular Research* 1994; vol. 28:1815–1820.

Fisher, et al. "Inhibition of osteoclastic bone resorption in vivo by echistatin, an 'arginyl–glycyl–aspartyl' (RDG)–containing protein", *Endocrinology*, vol. 132:3 1411–13, 1993.

Sato, et al. "Echistatis is a potent inhibitor of bone resorption in culture" *J. Cell Bio.*, vol. 111, Oct. 1990 1713–1723.

Horton, et al. "Arg–Gly–Asp (RGD) peptides and Anti–Vitronectin Receptor Antibody", *Experimental Cell Research*, vol. 195, 368–375 (1991).

Brooks, et al. "Integrin $\alpha_v\beta_3$ antagonists promote tumor regression by inducing apoptosis", *Cell*, vol. 79, 1157–1164 (Dec. 1994).

*Primary Examiner*—Brenda Coleman
(74) *Attorney, Agent, or Firm*—Foley & Lardner

(57) ABSTRACT

There are described cycloalkyl derivatives of the formula (I)

$$R^1—Y—A—B—D—E—F—G \qquad (I)$$

in which $R^1$, Y, A, B, D, E, F and G have the meaning indicated herein, their preparation and their use as medicaments. The compounds according to the invention can be used as vitronectin receptor antagonists and as inhibitors of bone resorption.

14 Claims, No Drawings

CYCLOALKYL DERIVATIVES AS INHIBITORS OF BONE RESORPTION AND VITRONECTIN RECEPTOR ANTAGONISTS

This application is a continuation of application Ser. No. 08/899,503, filed Jul. 24, 1997 now abandoned.

BACKGROUND OF THE INVENTION

1) Field of the Invention

The present invention relates to compounds of the formula I and their physiologically tolerable salts. The present invention also relates to pharmaceutical preparations comprising such compounds, their preparation and use as medicaments, in particular as inhibitors of bone resorption by osteoclasts, as inhibitors of tumor growth and tumor metastasis, as antiinflammatories, for the treatment or prophylaxis of cardiovascular disorders such as arteriosclerosis or restenosis, for the treatment or prophylaxis of nephropathies and retinopathies, such as, for example, diabetic retinopathy, and as vitronectin receptor antagonists for the treatment and prophylaxis of illnesses which are based on the interaction between vitronectin receptors and their ligands in cell-cell or cell-matrix interaction processes. The invention furthermore relates to the use of the compounds of the formula I and their physiologically tolerable salts and pharmaceutical preparations comprising such compounds as medicaments for the alleviation or cure of illnesses which are caused at least partially by an undesired extent of bone resorption, angiogenesis, or proliferation of cells of the vascular smooth musculature.

2) Description of Related Art

Human bones undergo a continuous dynamic renovation process which involves bone resorption and bone formation. These processes are controlled by types of cell specialized for this. Bone formation is based on the deposition of bone matrix by osteoblasts, bone resorption is based on the degradation of bone matrix by osteoclasts. The majority of bone disorders are based on a disturbed equilibrium between bone formation and bone resorption. Osteoporosis is characterized by a loss of bone matrix. Activated osteoclasts are polynuclear cells having a diameter of up to 400 $\mu$m, which remove bone matrix. Activated osteoclasts accumulate on the surface of the bone matrix and secrete proteolytic enzymes and acids into the so-called "sealing zone", the region between their cell membrane and the bone matrix. The acid environment and the proteases bring about the degradation of the bone.

Studies have shown that the accumulation of osteoclasts on the bone is controlled by integrin receptors on the cell surface of osteoclasts.

Integrins are a superfamily of receptors which include, inter alia, the fibrinogen receptor $\alpha_{IIb}\beta_3$ on the blood platelets and the vitronectin receptor $\alpha_V\beta_3$. The vitronectin receptor $\alpha_V\beta_3$ is a membrane glycoprotein which is expressed on the cell surface of a number of cells such as endothelial cells, cells of the vascular smooth musculature, osteoclasts and tumor cells. The vitronectin receptor $\alpha_V\beta_3$ which is expressed on the osteoclast membrane controls the process of accumulation on the bone and bone resorption and thus contributes to osteoporosis.

$\alpha_V\beta_3$ in this case binds to bone matrix proteins such as osteopontin, bone sialoprotein and thrombospontin, which contain the tripeptide motif Arg-Gly-Asp (or RGD).

Horton and co-workers describe RGD peptides and an anti-vitronectin receptor antibody (23C6), which inhibit tooth destruction by osteoclasts and the migration of osteoclasts (Horton et al., Exp. Cell. Res. 1991, 195, 368). In J. Cell Biol. 1990, 111, 1713, Sato et al. describe echistatin, an RGD peptide from snake venom, as a potent inhibitor of bone resorption in a tissue culture and as an inhibitor of osteoclast attachment to the bone. Fischer et al. (Endocrinology, 1993, 132, 1411) were able to show in the rat that echistatin also inhibits bone resorption in vivo.

The vitronectin receptor $\alpha_V\beta_3$ on human cells of the vascular smooth musculature of the aorta stimulates the migration of these cells into the neointima, which finally leads to arteriosclerosis and restenosis after angioplasty (Brown et al., Cardiovascular Res. 1994, 28, 1815).

Brooks et al. (Cell 1994, 79, 1157) show that antibodies against $\alpha_V\beta_3$ or $\alpha_V\beta_3$ antagonists can bring about a shrinkage of tumors by inducing the apoptosis of blood vessel cells during angiogenesis. Chersh et al. (Science 1995, 270, 1500) describe anti-$\alpha_V\beta_3$ antibodies or $\alpha_V\beta_3$ antagonists which inhibit bFGF-induced angiogenesis processes in the rat eye, which could be useful therapeutically in the treatment of retinopathies.

The Patent Application WO 94/12181 describes substituted aromatic or nonaromatic ring systems and WO 94/08577 describes substituted heterocycles as fibrinogen receptor antagonists and inhibitors of platelet aggregation. EP-A-518 586 and EP-A-528 587 disclose aminoalkyl- or heterocyclyl-substituted phenylalanine derivatives, and WO 95/32710 discloses aryl derivatives as inhibitors of bone resorption by osteoclasts. WO 96/100574 describes benzodiazepines, and WO 96/100730 describes fibrinogen receptor antagonist templates, in particular benzodiazepines which are linked to a nitrogen-bearing 5-membered ring, as vitronectin receptor antagonists.

SUMMARY OF THE INVENTION

One object of the present invention is to provide compounds and their pharmacologically tolerable salts capable of being used as inhibitors of bone resorption by osteoclast, as inhibitors of tumor growth and tumor metastasis, as antiinflammatories, for the treatment or prophylaxis of cardiovascular disorders such as arteriosclerosis or restenosis, for the treatment or prophylaxis of nephropathies and retinopathies and as vitronectin receptor antagonists for the treatment and prophylaxis of illnesses which are based on the interaction between vitronectin receptors and their ligands in cell-cell or cell-matrix interaction processes. Another object of the invention is to provide compounds which can be used as carriers for active compounds in order to transfer the active compounds specifically to the site of action.

Another object of the invention is to provide a pharmaceutical preparation which includes the compound of the present invention. Still another object of the invention is to provide methods for the production of the compound of the present invention. Still another object of the present invention is to provide methods for the treatment of the conditions described above.

In accomplishing the foregoing objects, there has been provided according to one aspect of the present invention, cycloalkyl derivatives of the formula I

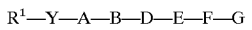    I in which:

A is a direct bond, $(C_1-C_8)$-alkanediyl, $-NR^2-C(O)-NR^2-$, $-NR^2-C(O)O-$, $-NR^2-C(O)S-$, —NR²—C(S)—NR²—, —NR²—C(S)—O—, —NR²—C(S)—S—, —NR²—S(O)$_n$—NR²—, —NR²—S(O)$_n$—O—, —NR²—S(O)$_n$—, $(C_3-C_{12})$—cycloalkanediyl, —C≡C—, —NR²—C(O)—, —C(O)—NR²—, —$(C_5-C_{14})$—arylene-C(O)—NR²—, —O—, —S(O)$_n$—, —$(C_5-C_{14})$-arylene-, —CO—, —$(C_5-C_{14})$-arylene-CO—, —NR²—, —SO₂—NR²—, —CO₂—, —CR²=CR³—, —$(C_5-C_{14})$—arylene-S(O)$_n$—, which in each case can be mono- or disubstituted by $(C_1-C_8)$-alkanediyl, such as, for example, —$(C_1-C_8)$—alkanediyl —CO—NR²—$(C_1-C_8)$—alkanediyl, —$(C_1-C_8)$-alkanediyl-CO—NR²—$(C_1-C_8)$-alkanediyl;

B is a direct bond, $(C_1-C_{10})$-alkanediyl, —CR²=CR³— or —C≡C—, which in each case can be mono- or disubstituted by $(C_1-C_8)$-alkanediyl, such as, for example, —CH₂—CR²=CR³—;

D is a direct bond, $(C_1-C_8)$-alkanediyl, —O—, —NR²—, —CO—NR²—, —NR²—CO—, —NR²—C(O)—NR²—, —NR²—C(S)—NR²—, —OC(O)—, —C(O)O—, —CO—, —CS—, —S(O)—, —S(O)₂—, —S(O)₂—NR²—S(O)—, —NR²—S(O)₂—, —S—, —CR²=CR³—, —C≡C—, or —CH(OH)—, which in each case can be mono- or disubstituted by $(C_1-C_8)$-alkanediyl;

E is a 6-membered aromatic ring system, which optionally contains up to 4 nitrogen atoms and is optionally substituted by 14 identical or different radicals from the group consisting of R², R³, fluorine, Cl, Br, I, NO₂, and OH;

F is defined as D;

G is

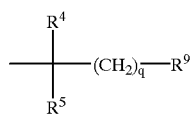

Y is a direct bond or —NR²—;

R¹ is R²—C(=NR²)—NR²—, R²R³N—C(=NR²)—, R²R³N—C(=NR²)—NR²—, or a 4–10—membered mono- or polycyclic aromatic or nonaromatic ring system, which can optionally contain 1–4 heteroatoms from the group consisting of N, O and S and can optionally be monosubstituted or polysubstituted by substituents from the group consisting of R¹¹, R¹², R¹³ and R¹⁴;

R², R³ independently of one another are H, $(C_1-C_{10})$-alkyl which is optionally mono- or polysubstituted by fluorine, $(C_3-C_{12})$-cycloalkyl, $(C_3-C_{12})$-cycloalkyl-$(C_1-C_8)$-alkanediyl, $(C_5-C_{14})$-aryl, $(C_1-C_{14})$-aryl-$(C_1-C_8)$-alkanediyl, H₂N, (R⁸O)R⁸NR⁷, R⁸OR⁷, R⁸OC(O)R⁷, R⁸—$(C_5-C_{14})$-arylene-R⁷, R⁸OR⁷, H⁸—$(C_5-C_{14})$-arylene-R⁷, R⁸R⁸NR⁷, HO—$(C_1-C_8)$-alkanediyl-NR⁸R⁷, R⁸R⁸NC(O)R⁷, R⁸C(O)NR⁸R⁷, R⁸C(O)R⁷, R⁸R⁸N—C(=NR⁸)—, R⁸R⁸N—C(=NR⁸)—NR⁸— or $(C_1-C_{18})$-alkylcarbonyloxy-$(C_1-C_6)$—alkanediyloxycarbonyl;

R⁴ is $(C_{10}-C_{18})$-cycloalkyl, $(C_{10}-C_{18})$-cycloalkyl-$(C_1-C_8)$-alkanediyl, it being possible for the cycloalkyl radicals to be mono- or polycyclic, saturated or mono- or polyunsaturated and to be substituted as described in the case of R⁶, or R⁶OR⁷, R⁶CO₂R⁷, R⁶OC(O)R⁷, R⁶—$(C_5-C_{14})$-arylene-R⁷, R⁶N(R²)R⁷, R⁶R⁸NR⁷, R⁶N(R²)C(O)OR⁹, R⁶S(O)$_n$N(R²)R⁷, R⁶OC(O)N(R²)R⁷, R⁶C(O)N(R²)R⁷, R⁶N(R²)C(O)N(R²)R⁷, R⁶N(R²)S(O)$_N$(R²)R⁷, R⁶S(O)$_n$R⁷, R⁶SC(O)N(R²)R⁷, R⁶C(O)R⁷, R⁶N(R²)C(O)R⁷, R⁶N(R²)S(O)$_n$R⁷;

R⁵ is H, fluorine, $(C_1-C_8)$-alkyl, $(C_3-C_{12})$-cycloalkyl, $(C_3-C_{12})$-cycloalkyl-$(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, it being possible for the alkyl radicals to be mono- or polysubstituted by fluorine;

R⁶ is $(C_{10}-C_{18})$-cycloalkyl, $(C_{10}-C_{18})$-cycloalkyl-$(C_1-C_8)$-alkanediyl, it being possible for the cycloalkyl radicals to be mono- or polycyclic, saturated or mono- or polyunsaturated, and mono- or polysubstituted by $(C_1-C_{10})$-alkyl which is optionally mono- or poly-substituted by fluorine, $(C_3-C_{12})$-cycloalkyl, $(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, $(C_1-C_8)$-alkoxy, $(C_5-C_{14})$-aryl-$(C_1-C_8)$-alkanediyloxy, $(C_5-C_{14})$-aryloxy, $(C_1-C_8)$-alkylcarbonyloxy-$(C_1-C_4)$-alkanediyloxy, NH₂, mono- or di-$(C_1-C_8$-alkyl)-amino, $(C_5-C_{14})$-aryl-$(C_1-C_8)$-alkanediylamino, $(C_5-C_{14})$-arylamino, =O, =S, NO₂, OH, fluorine, Cl, Br, or I;

R⁷ is a direct bond or $(C_1C_8)$-alkanediyl;

R⁸ is H, $(C_1C_8)$-alkyl, $(C_3-C_{12})$-cycloalkyl, $(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, it being possible for the alkyl radicals to be mono- or polysubstituted by fluorine;

R⁹ is $C(O)R^{10}$, $C(S)R^{10}$, $S(O)_n R^{10}$, $P(O)(R^{10})_n$ or a four- to eight-membered, saturated or unsaturated heterocycle which contains 1, 2, 3 or 4 heteroatoms from the group N, O, S, such as, for example, tetrazolyl, imidazolyl, pyrazolyl, oxazolyl, thiadiazolyl;

R¹⁰ is OH, $(C_1-C_8)$-alkoxy, $(C_5-C_{14})$-aryl-$(C_1-C_8)$-alkanediyloxy, $(C_5-C_{14})$-aryloxy, $(C_1-C_8)$-alkylcarbonyloxy-$(C_1-C_4)$-alkanediyloxy, $(C_5-C_{14})$-aryl-$(C_1-C_8)$-alkanediylcarbonyloxy-$(C_1-C_5)$-alkanediyloxy, NH₂, mono- or di-$(C_1-C_8$-alkyl)-amino, $(C_5-C_{14})$-aryl-$(C_1-C_8)$-alkanediylamino, $(C_1-C_8)$-dialkylaminocarbonylmethylenoxy, $(C_5-Cl_{14})$-aryl-$(C_1-C_8)$-dialkylaminocarbonylmethylenoxy or $(C_5-C_{14})$-arylamino or a radical of an L- or D-amino acid;

R¹¹, R¹², R¹³, R¹⁴ independently of one another are H, $(C_1-C_{10})$-alkyl, which is optionally mono- or polysubstituted by fluorine, $(C_3-C_{12})$-cycloalkyl, $(C_3-C_{12})$-cycloalkyl-$(C_1-C_8)$-alkanediyl, $(C_5-C_{14})$-aryl, $(C_5-C_{14})$-aryl-$(C_1-C_8)$-alkanediyl, H₂N, (R⁸O)R⁸NR⁷, R⁸OR⁷, R⁸OC(O)R⁷, R⁸R⁸NR⁷, R⁸—$(C_5-C_{14})$-arylene-R⁷, HO—$(C_{1-C8})$-alkanediyl-N(R²)R⁷, R⁸N(R²)C(O)R⁷, R⁸N(R²)C(O)R⁷, R⁸C(O)N(R²)R⁷, R⁸C(O)R⁷, R²R³N—C(=NR²)—NR²—, R²R³N—C(=NR²)—, =O, =S;

n is 1 or 2;

q is 0 or 1;

in all their stereoisomeric forms and mixtures thereof in any ratio; and their physiologically tolerable salts.

According to another aspect of the present invention, there has been provided a pharmaceutical preparation comprising at least one compound of the formula I and/or a physiologically tolerable salts thereof and at least one pharmaceutically innocuous excipient and/or additive.

According to still another aspect of the present invention, there has been provided a process for the preparation of a compound of the formula I,

R¹³—Y—A—B—D—E—F—G    I, in which F is —C(O)NR²— and R¹, R², Y, A, B, D, E and G are defined as above, which comprises carrying out a fragment condensation with a compound of the formula II

R¹—Y—A—B—D—E—M    II, where M is hydroxycarbonyl, $(C_1-C_6)$-alkoxycarbonyl or activated carboxylic acid derivatives and R¹, Y, A, B, D and E have the abovementioned meaning, and HNR²—G, in which R² and G are as defined above.

According to yet another aspect of the present invention, there has been provided a process for the preparation of a compound of the formula I,

R¹³—Y—A—B—O—E—F—G    I, in which R¹—Y—A— is

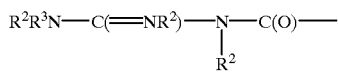

or a cyclic acylguanidine of the type

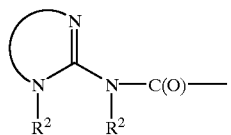

and R², R³, B, D, E, F and G are defined as above, which comprises reacting a compound of the formula III

Q(O)C—B—D—E—F—G    III in which Q is an easily nucleophilically substitutable leaving group and B, D, E, F and G are as defined above, with the appropriate guanidine (derivative) of the type

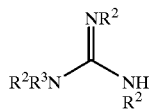

or the cyclic guanidine (derivative)

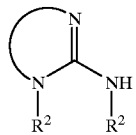

in which R² and R³ are as defined above.

According to another aspect of the present invention, there has been provided a method for inhibiting bone resorption by osteoclasts, inhibiting tumor growth and tumor metastasis, reducing inflammation, treating or preventing cardiovascular disorders, for treating or preventing nephropathies and retinopathies or for the treatment and prevention of diseases which are based on the interaction between vitronectin receptors and their ligands in cell-cell or cell-matrix interaction processes, comprising administering a therapeutically effective amount of the compound of the formula I and/or a physiologically tolerable salt thereof to a human or animal in need thereof.

Further objects, features and advantages of the present invention will become apparent from the detailed description of preferred embodiments which follows.

DETAILED DESCRIPTION OF PREFERRED EMBODIMENTS

The alkyl radicals occurring in the substituents of the compound of formula I can be straight-chain or branched, saturated or mono- or polyunsaturated. The same applies to radicals derived therefrom, such as, for example, alkoxy.

Cycloalkyl radicals in $R^2$, $R^3$, $R^5$, $R^8$ and $R^{11}{}_{-R}{}^{14}$ can be mono-, bi- or tricyclic.

Monocyclic cycloalkyl radicals in $R^2$, $R^3$, $R^5$, $R^8$ and $R^{11}-R^{14}$ can include, in particular, cyclopropyl, cyclobutyl, cyclopentyl, cyclohexyl, cycloheptyl and cyclooctyl, which, however, can also be substituted by, for example, $(C_1-C_4)$-alkyl.

Examples of substituted cycloalkyl radicals which may be mentioned are 4-methylcyclohexyl and 2,3-dimethylcyclopentyl. Examples of parent substances of monocyclic $(C_{10}-C_{18})$-cycloalkyl radicals in $R^4$ and $R^6$ are, for example, cyclodecane or cyclododecane.

Bicyclic and tricyclic cycloalkyl radicals in $R^2$, $R^3$, $R^5$, $R^8$ and $R^{11}-R^{14}$ can be unsubstituted or substituted in any desired suitable positions by one or more oxo groups and/or one or more identical or different $(C_1-C_4)$-alkyl groups, e.g. methyl or isopropyl groups, preferably methyl groups. Bicyclic and tricyclic $(C_{10}-C_{18})$-cycloalkyl radicals in $R^4$ and $R^6$ can be substituted as described there. The free bond of the bi- or the tricyclic radical can be located in any desired position in the molecule; the radical can thus be bonded via a bridgehead atom or an atom in a bridge. The free bond can also be located in any desired stereochemical position, for example in an exo- or an endo-position.

An example of a bicyclic ring system is decalin (decahydronaphthalene), an example of a system substituted with an oxo group is 2-decalone.

Examples of parent substances of tricyclic systems are twistane (=tri-cyclo[$4.4.0.0^{3.8}$]decane), adamantane (=tricyclo[$3.3.1.1^{3.7}$]decane), noradamantane (=tricyclo[$3.3.1.0^{3.7}$]nonane), tricyclo[$2.2.1.0^{2.6}$]heptane, tricyclo[$5.3.2.0^{4.9}$]dodecane, tricyclo[$5.4.0.0^{2.9}$]undecane or tricyclo[$5.5.1.^{3.11}$]tridecane.

Examples of parent substances of tricyclic $(C_{10}-C_{18})$-cycloalkyl radicals in $R^4$ and $R^6$ are twistane (=tricycio[$4.4.0.0^{3.8}$]decane), adamantane (=tricyclo[$3.3.1.1^{3.7}$]decane), noradamantane (=tricyclo[$3.3.1.0^{3.7}$]-nonane), tricyclo[$5.3.2.0^{4.9}$]dodecane, tricyclo[$5.4.0.0^{2.9}$]undecane or tricyclo[$5.5.1.0^{3.1}$]tridecane.

Examples of 6-membered aromatic ring systems are phenyl, pyridyl, pyridazinyl, pyrimidinyl, pyrazinyl, 1,3,5-triazinyl, 1,2,4-triazinyl, 1,2,3-triazinyl, tetrazinyl.

Aryl is, for example, phenyl, naphthyl, biphenylyl, anthryl or fluorenyl, 1-naphthyl, 2-naphthyl and in particular phenyl being preferred. Aryl radicals, in particular phenyl radicals, can be mono- or polysubstituted, preferably mono-, di- or trisubstituted, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, cyano hydroxycarbonyl, aminocarbonyl, $(C_1-C_4)$-alkoxycarbonyl, phenyl, phenoxy, benzyl, benzyloxy, tetrazolyl, $(R^{17}O)_2P(O)$— and $(R^{17}O)_2P(O)$—O—, where $R^{17}$ is H, $(C_1-C_{10})$-alkyl, $(C_6-C_{14})$-aryl or $(C_6-C_{14})$-aryl-$(C_1-C_8)$-alkyl.

In monosubstituted phenyl radicals, the substituent can be located in the 2-, the 3- or the 4-position, with the 3- and the 4-position being preferred. If phenyl is disubstituted, the substituents can be in the 1,2-, 1,3- or 1,4-position relative to one another. Preferably, in disubstituted phenyl radicals the two substituents are arranged in the 3- and the 4-position. relative to the linkage site.

Aryl groups can furthermore be mono- or polycyclic aromatic ring systems in which 1 to 5 carbon atoms can be replaced by 1 to 5 heteroatoms, such as, for example, 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a benzo-fused, cyclopenta-, cyclohexa- or cyclohepta-fused derivative of these radicals. These heterocycles can be substituted by the same substituents as the abovementioned carbocyclic aryl systems.

In the series of these aryl groups, mono- or bicyclic aromatic ring systems having 1–3 heteroatoms from the group consisting of N, O, S, are preferred, which can be substituted by 1–3 substituents from the group consisting of $(C_1–C_6)$-alkyl, $(C_1–C_6)$-alkoxy, fluorine, Cl, $NO_2$, $NH_2$, trifluoromethyl, OH, $(C_{1-C4})$-alkoxycarbonyl, phenyl, phenoxy, benzyloxy or benzyl.

Particularly preferred in this case are mono- or bicyclic aromatic 5–10-membered ring systems having 1–3 heteroatoms from the series N, O, S, which can be substituted by 1–2 substituents from the group consisting of $(C_1–C_4)$-alkyl, $(C_1–C_4)$-alkoxy, phenyl, phenoxy, benzyl or benzyloxy.

L- or D-amino acids can be natural or unnatural amino acids. α-Amino acids are preferred. Examples which may be mentioned are (cf. Houben-Weyl, Methoden der organischen Chemie [Methods of Organic Chemistry], Volume XV/1 and 2, Georg Thieme Verlag, Stuttgart, 1974):

Aad, Abu, γAbu, ABz, 2ABz, eAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab. Dadd, Dap, Dapm, Dasu, Dien, Dpa, Dtc, Fel, Gin, Glu, Gly, Guv, hAla, hArg, hCys, hGln, hGlu, His, hile, hLeu, hLys, hMet, hPhe, hPro, hSer, hThr, hTrp, hTyr, Hyl, Hyp, 3Hyp, lie, Ise, Iva, Kyn, Lant, Lcn, Leu, Lsg, Lys, βLys, ΔLys, Met, Mim, Min, nArg, Nie, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tie, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl) aminoacetic acid.

The amino acids can furthermore include:
pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicycto[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxyl[2.2.1]heptane)-2,3-pyrrolidine-5-carboxylic acid; spiro(bicyclo[2.2.2] octane)-2,3-pyrrolidine-5-carboxylic acid; 2-azatricyclo[4.3.0.1$^{6.9}$]decane-3carboxylic acid; decahydrocyclohepta-[b]pyrrole-2-carboxylic acid; decahydrocycloocta[c]pyrrole2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole4-carboxylic acid; isoxazolidine-3-carboxylic acid; pyrazolidine3-carboxylic acid, hydroxypyrrolidine-2-carboxylic acid, all of which can be optionally substituted (see following formulae):

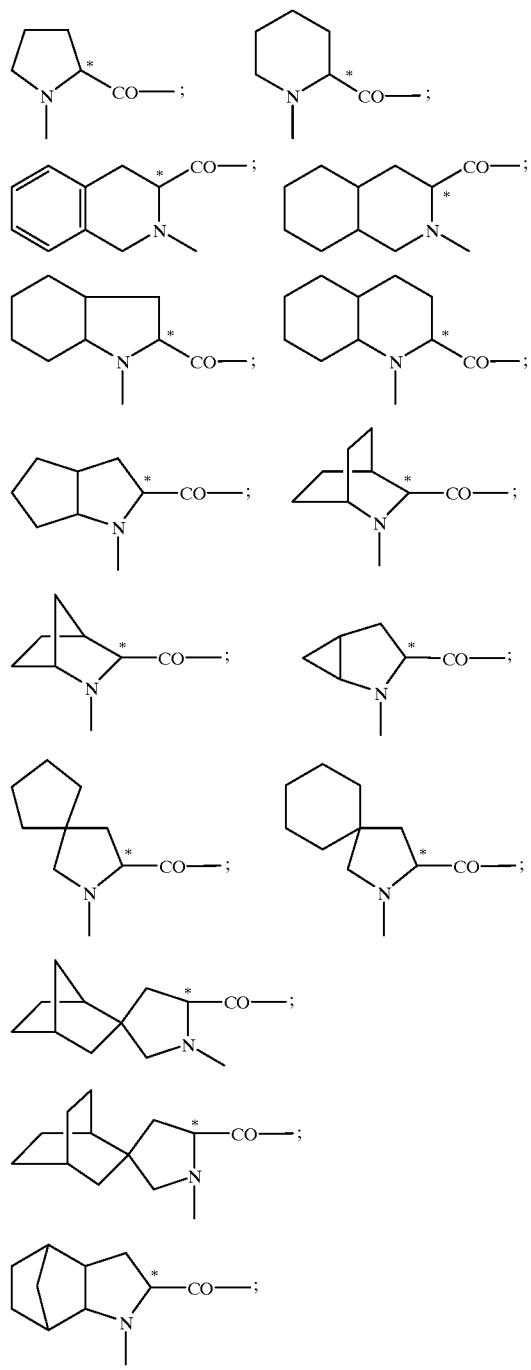

-continued

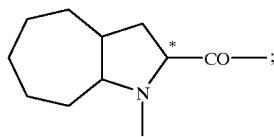

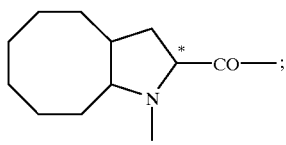
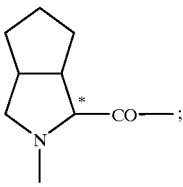

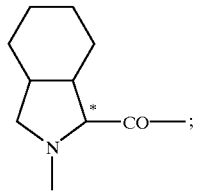
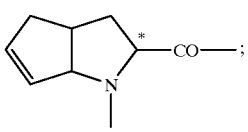

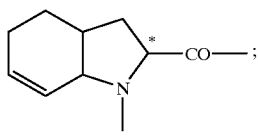
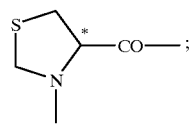

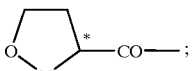
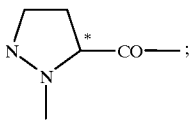

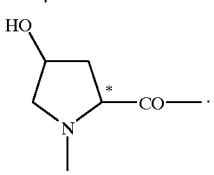

The heterocycles on which the abovementioned radicals are based are disclosed, for example, in U.S. Pat. No. 4,344,949; U.S. Pat. No. 4,374,847; U.S. Pat. No. 4,350,704; EP-A 29,488: EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

The amino acids can furthermore also be present as esters or amides, such as, for example, the methyl ester, ethyl ester, isopropyl ester, isobutyl ester, tert-butyl ester, benzyl ester, ethyl amide, semicarbazide or ω-amino-$(C_2-C_8)$-alkyl amide.

Functional groups of the amino acids can be present in protected form. Suitable protective groups such as, for example, urethane protective groups, carboxyl protective groups and side chain protective groups are described in Hubbuch, Kontakte (Merck) 1979, No. 3, pages 14 to 23 and in Bullesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-butyl, OBzl, ONbzl, OMbzl, Bzl, Mob, Pic, Trt.

Physiologically tolerable salts of the compounds of the formula I are, in particular, pharmaceutically utilizable or nontoxic salts. Such salts are formed, for example, from compounds of the formula I which contain acidic groups, e.g. carboxyl, with alkali metals or alkaline earth metals, such as, for example, Na, K, Mg and Ca, and with physiologically tolerable organic amines, such as, for example, triethylamine, ethanolamine or tris(2-hydroxyethyl) amine. Compounds of the formula I which contain basic groups, e.g. an amino group, an amidino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid, methanesulfonic acid or p-toluenesulfonic acid.

The compounds of the formula I according to the invention can contain optically active carbon atoms which independently of one another can have R or S configuration and can thus be present in the form of pure enantiomers or pure diastereomers or in the form of enantiomer mixtures or diastereomer mixtures. The present invention relates both to pure enantiomers and enantiomer mixtures and to diastereomers and diastereomer mixtures. The invention covers mixtures of two stereoisomers and of more than two stereoisomers of the formula I and all ratios of stereoisomers in the mixtures.

If A, D and F independently of one another are $—CR^2=CR^3—$, the compounds of the formula I according to the invention can be present as E/Z isomer mixtures. The present invention relates to both pure E and Z isomers and to mixtures of E/Z isomers in all ratios. Diastereomers, including E/Z isomers, can be separated into the individual isomers by chromatography. Racemates can either be separated into the two enantiomers by chromatography on chiral phases or by resolution.

The compounds of the formula I according to the invention can moreover contain mobile hydrogen atoms, i.e. be present in various tautomeric forms. The present invention also relates to these tautomers.

Preferred compounds of the formula I are those in which:

A is a direct bond, $(C_1-C_6)$-alkanediyl, $—NR^2—C(O)—NR^2—$, $—NR^2—C(O)O—$, $—NR^2—C(O)_n—$, $—NR^2—C(S)—N R^2—$, $—N R^2—C(S)—O—$, $NR^2—C(S)—S—$, $—N R^2—S(O)_n—NR^2—$, $—NR^2—S(O)_n—O—$, $—NR^2—S(O)_n—$, $(C_3-C_8)$-cycloalkanediyl, $—C\equiv C—$, $—NR^2—C(O)—$, $C(O)—NR^2—$, $—(C_5-C_{12})$-arylene-$C(O)—NR^2—$, $—O—$, $—S(O)_n—$, $—(C_5-C_{12})$-arylene-, $—CO—$, $—(C_5-C_{12})$-arylene-CO—, $—NR^2—$, $—SO_2—NR^2—$, $—CO_2—$, $—CR^2=CR^3—$, $—(C_5-C_{12}$-arylene-$S(O)_n—$, which in each case can be mono- or disubstituted by $(C_{1-C8})$-alkanediyl;

B is a direct bond, $(C_1-C_8)$-alkanediyl, $—CR^2=CR^3—$, or $—C\equiv C—$, which in each case can be mono- or disubstituted by $(C_1-C_8)$-alkanediyl;

D is a direct bond, $(C_1-C_8)$-alkanediyl or $—O—$, $—NR^2—$, $—CO—NR^2—$, $—NR^2—CO—$, $—NR^2—C(O)—NR^2—$, $—NR^2—C(S)—NR^2—$, $—OC(O)—$, $—C(O)O—$, $—CO—$, $—CS—$, $—S(O)—$, $—S(O)_2—$, $—S(O)_2—NR^2—$, $—NR^2—S(O)—$, $—NR^2—C(S)—NR^2—S(O)_2—$, $—S—$, $—CR^2=CR^3—$, $—C\equiv C—$, which in each case can be mono- or disubstituted by $(C_1-C_6)$-alkanediyl;

E is a 6-membered aromatic ring system, which optionally contains 1 or 2 nitrogen atoms and is optionally substituted by 1–3 identical or different radicals from the group consisting of $R^2$, $R^3$, fluorine, Cl and OH;

F is defined as D;

G is

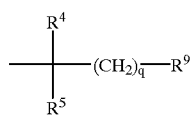

Y is a direct bond or —NR$^2$—;

R$^1$ is R$^2$—C(=NR$^2$)—NR$^2$—, R$^2$R$^3$N—C(=NR$^2$)—, NR$^2$—, or 4–10-membered mono- or polycyclic aromatic or nonaromatic ring system which can optionally contain 1–4 heteroatoms from the group consisting of N, O and S and can optionally be monosubstituted or polysubstituted by substituents from the group consisting of R$^{11}$, R$^{12}$, R$^{13}$ and R$^{14}$;

R$^2$, R$^3$ independently of one another are H, (C$_1$–C$_8$)-alkyl which is optionally mono- or polysubstituted by fluorine, (C$_3$–C$_8$)-cycloalkyl, (C$_3$–C$_8$)-cycloalkyl-(C$_3$–C$_6$)-alkanediyl, (C$_5$–C$_{12}$)-aryl, (C$_5$–C$_{12}$)-aryl-(C$_1$–C$_6$)-alkanediyl, H$_2$N, (R$^8$O)R$^8$), NR$^7$, R$^8$OR$^7$, R$^8$OC(O)R$^7$, R$^8$—(C$_5$–C$_{12}$)-arylene-R$^7$, R$^8$R8N—, HO—(C$_1$–C$_8$)-alkanediyl-NR$^8$R$^7$, R$^8$R$^8$R$^8$NC(O)R$^7$, R$^8$C(O)NR$^8$R$^7$, R$^8$C(O)R$^7$, R$^8$R$^8$N—C(=NR$^8$)—, R$^8$R$^8$N—C(=NR$^8$)—NR$^8$— or (C$_1$–C$_8$)-alkylcarbonyloxy-(C$_1$–C$_4$)-alkanediyloxycarbonyl;

R$^4$ is (C$_{10}$–C$_{16}$)-cycloalkyl, (C$_{10}$–C$_{16}$)-cycloalkyl-(C$_1$–C$_8$)-alkanediyl, it being possible for the cycloalkyl radicals to be mono- or polycyclic, saturated or mono- or polyunsaturated and to be substituted as described in the case of R$^6$, or R$^6$OR$^7$, R$^6$SR$^7$, R$^6$CO$_2$R$^7$, R$^6$OC(O)R$^7$, R$^6$—(C$_5$–C$_{12}$)-arylene-R$^7$, R$^6$R$^8$NR$^7$, R$^6$N(R$^2$)C(O)OR$^7$, R$^6$S(O)$_n$N(R$^2$)R$^7$, R$^6$OC(O)N(R$^2$)R$^7$, R$^6$C(O)N(R$^2$)R$^7$, R$^6$N(R$^2$)C(O)N(R$^2$)R$^7$, R$^6$N(R$^2$)S(O)$_n$N(R$^2$)R$^7$, R$^6$S(O)$_n$R$^7$, R$^6$SC(O)N(R$^2$)R$^7$, R$^6$C(O)R$^7$, R$^6$N(R$^2$)C(O)R$^7$, R$^6$N(R$^2$)S(O)$_n$R$^7$;

R$^5$ is H, (C$_1$–C$_6$)-alkyl, (C$_3$–C$_8$)-cycloalkyl, (C$_3$–C$_8$)-cycloalkyl-(C$_1$–C$_8$)-alkanediyl, (C$_5$–C$_{10}$)-aryl, (C$_5$–C$_{10}$)-aryl-(C$_1$–C$_6$)-alkanediyl, it being possible for the alkyl radicals to be mono- or polysubstituted by fluorine;

R$^6$ is (C$_{10}$–C$_{16}$)-cycloalkyl, (C$_{10}$–C$_{16}$)-cycloalkyl-(C$_1$–C$_6$)-alkanediyl, it being possible for the cycloalkyl radicals to be bi- or tricyclic, saturated or mono- or polyunsaturated, and mono- or polysubstituted by (C$_1$–C$_8$)-alkyl, which is optionally mono- or polysubstituted by fluorine, (C5–C$_6$)-cycloalkyl, (C$_5$–C$_6$)-cycloalkyl, (C$_5$–C$_6$)-cycloalkyl-(C$_1$–C$_6$)-alkanediyl, (C$_5$–C$_{10}$)-aryl, (C$_5$–C$_{10}$)-aryl-(C$_1$–C$_6$)-alkanediyl, (C$_1$–C$_6$)-alkoxy, (C$_5$–C$_{10}$)-aryloxy, (C$_5$–C$_{10}$)-aryl-(C$_1$–C$_6$)-alkanediyloxy, NH$_2$, mono- or di-(C$_1$–C$_6$)-alkyl)-amino, =O, OH, fluorine or Cl;

R$^7$ is a direct bond or (C$_1$–C$_6$)-alkanediyl;

R$^8$ is H, (C$_1$–C$_6$)-alkyl, (C$_3$–C$_8$)-cycloalkyl, (C$_3$–C$_8$)-cycloalkyl-(C$_1$–C$_6$)-alkanediyl, (C$_5$–C$_{12}$)-aryl, (C$_5$–C$_{12}$)-aryl-(C$_1$–C$_6$)-alkanediyl, it being possible for the alkyl radicals to be mono- or polysubstituted by fluorine;

R$^9$ is C(O)R$^{10}$, C(S)R$^{10}$, S(O)$_n$R$^{10}$, P(O)(R$^{10}$)$_n$ or a four to eight-membered, saturated or unsaturated heterocycle which contains 1, 2, 3 or 4 heteroatoms from the group consisting of N, O, S;

R$^{10}$ is OH, (C$_1$–C$_6$)-alkoxy, (C$_5$–C$_{12}$)-aryl-(C$_1$–C$_6$)-alkanediyloxy, (C$_5$–C$_{12}$)-aryloxy, (C$_1$–C$_6$)-alkylcarbonyloxy-(C$_1$–C$_4$)-alkanediyloxy, (C$_5$–C$_{12}$)-aryl-(C$_1$–C$_6$)-alkanediylcarbonyloxy-(C$_1$–C$_6$)-alkanediyloxy, NH$_2$, mono- or di-(C$_1$–C$_6$-alkyl)-amino, (C$_5$–C$_{12}$)-aryl-(C$_1$–C$_6$)-alkanediylamino, (C$_1$–C$_6$)-dialkylaminocarbonyl-methylenoxy;

R$^{11}$, R$^{12}$, R$^{13}$, R$^{14}$ independently of one another are H, (C$_1$–C$_8$)-alkyl, which is optionally mono- or polysubstituted by fluorine, (C$_3$–C$_8$)-cycloalkyl, (C$_3$–C$_8$)-cycloalkyl-(C$_1$–C$_6$)-alkanediyl, (C$_5$–C$_{12}$)-aryl, (C$_5$–C$_{12}$)-aryl-(C$_1$–C$_6$)-alkanediyl, H$_2$N, (R$^8$O) R$^8$NR$^7$, R$^8$OR$^7$, R$^8$OC(O)R$^7$, R$^8$—(C$_5$–C$_{12}$)-arylene-R$^7$, R$^8$R$^8$NR$^7$, HO—(C$_1$–C$_8$)-alkyl-N(R$^2$) R$^7$, R$^8$N(R$^2$)C(O)R$^7$, R$^8$C(O)N(R$^2$)R$^7$, R$^8$C(O)R$^7$, R$^2$R$^3$N—C(=NR$^2$)—, R$^2$R$^3$N—C(=NR$^3$)—NR$^2$, =O, =S;

n is 1 or 2;

q is 0 or 1;

in all their stereoisomeric forms and mixtures thereof in any ratio; and their physiologically tolerable salts.

Particularly preferred compounds of the formula I are those in which:

A is a direct bond, (C$_1$–C$_6$)-alkanediyl, —NR$^2$—C(O)—NR$^2$—, —NR$^2$—C(O)O—, —NR$^2$—S(O)$_n$—NR$^2$—, —NR$_2$—S(O)$_{n—}$, $_{(C3}$–C$_6$)-cycloalkanediyl, —C≡C—, —NR$^2$—C(O)—, —C(O)—NR$^2$—, —O—, —CO—, —NR$^2$—, —CO$_2$—, —CR$^2$=CR$^3$—, which in each case can be mono- or disubstituted by (C$_1$–C$_6$)-alkanediyl;

B is a direct bond, (C$_1$–C6)-alkanediyl, —CR$^2$=CR$^3$—, which can be mono- or disubstituted by (C$_1$–C$_6$)-alkanediyl;

D is a direct bond, (C$_1$–C$_6$)-alkanediyl or —O—, —NR$^2$—, —NR$^2$—CO—, —C(O)—NR$^2$—, —NR$_2$—C(O)—NR$_2$—, —OC(O)—, —C(O)—, —S(O)$_2$—NR$_2$—, —NR$_2$—S(O)—, —NR$_2$—S(O)$_2$—, which in each case can be mono- or disubstituted by (C$_1$–C$_6$)-alkanediyl;

E is phenylene or pyridinediyl which is optionally substituted by 1–3 identical or different radicals from the group consisting of R$^2$ and R$^3$;

F is a direct bond, (C$_1$–C$_6$)-alkanediyl, or —O—, —CO—NR$^2$, —NR$^2$—CO—, —NR$^2$—C(O)—NR$^2$—, —OC(O)—, —C(O)O—, —CO—, —S(O)$_2$—, —S(O)$_2$—NR$^2$—, —NR$^2$—S(O)$_2$—, —CR$^2$=CR$^3$—, —C≡C—, which in each case can be mono- or disubstituted by (C$_1$–C$_6$)-alkanediyl;

G is

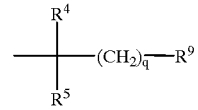

Y is a direct bond or —NH—;

R$^1$ is R$^2$—C(=NR$^2$)—NR$^2$—, R$^2$R$^3$N—C(=NR$^2$)—,

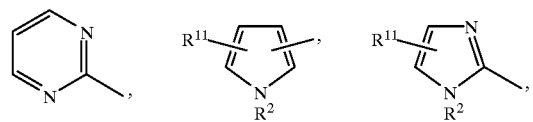

-continued

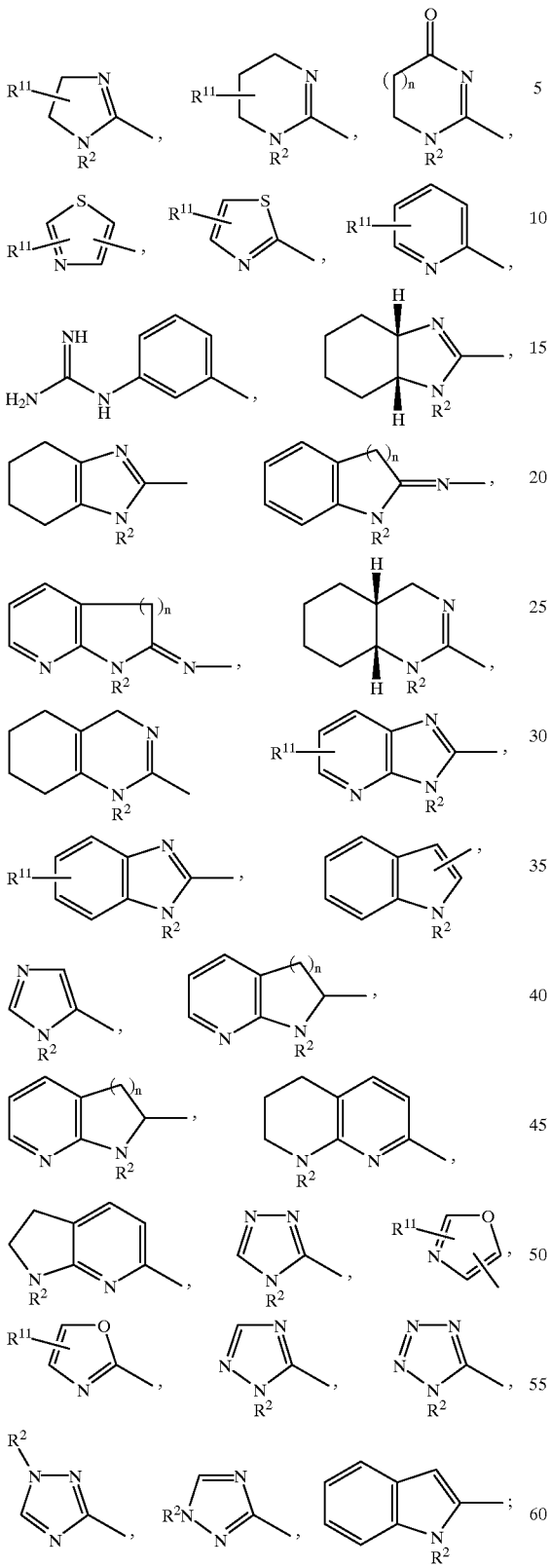

R², R³ independently of one another are H, (C₁–C₆)-
alkyl which is optionally mono- or polysubstituted,
preferably 1–6 times, by fluorine, (C₃–C₆)-
cycloalkyl, (C₃–C₆)-cycloalkyl-(C₁–C₄)-alkanediyl,
(C₅–C₁₀)-aryl-(C₅–C₁₀)-aryl-(C₁–C₄)-alkanediyl,
H₂N, R⁸OR⁷, R⁸—(C₅C₁₀)-arylene-R⁷, R⁸R⁸NR⁷,
R⁸NHC(O)R⁷, H₂N—C(=NH)—, H₂N—C
(=NH)—NH—;

R⁴ is (C₁₀–C₁₄)-cycloalky, (C₁₀–C₁₄)-cycloalkyl-
(C₁–C₆)-alkanediyl, it being possible for the
cycloalkyl radicals to be bi- or tricyclic, and to be
substituted 1–3 times by (C₁–C₆)-alkyl,
trifluoromethyl, pentafluoroethyl, phenyl, benzyl,
(C₁–C₆)-alkoxy, phenoxy, benzyloxy, NH₂, =O or
mono- or di-(C₁–C₆-alkyl)-amino; or R⁶OR⁷,
R⁶CO₂R⁷, R⁶OC(O)R⁷, R⁶NHR⁷, R⁶R⁸NR⁷,
R⁶NHC(O)OR⁷, R⁶S(O)ₙNHR⁷, R⁶C(O)NHR⁷, R⁶C
(O)NHR⁷, R⁶C(O)R⁷, R⁶NHC(O)NHR⁷, R⁶NHC
(O)R⁷;

R⁵ is H, (C₁–C₆)-alkyl, (C₅–C₆)-cycloalkyl, (C₅–C₆)-
cycloalkyl-(C₁–C₆)-alkanediyl, trifluoromethyl,
pentafluoroethyl, phenyl, benzyl;

R⁶ is (C₁₀–C₁₄)-cycloalkyl, (C₁₀–C₁₄)-cycloalkyl-
(C₁–C₈)-alkanediyl, it being possible for the
cycloalkyl radicals to be bi- or tricyclic, and to be
substituted 1–3 times by (C₁–C₆)-alkyl,
trifluoromethyl, pentafluoroethyl, phenyl, benzyl,
(C¹–C⁶)-alkoxy, phenoxy, benzyloxy, NH₂, =O or
mono- or di-(C₁–C₆-alkyl)-amino;

R⁷ is a direct bond or (C₁–C₆)-alkanediyl;

R⁸ is H, (C₁–C₆)-alkyl, (C₃–C₆)-cycloalkyl, (C₃–C₆)-
cycloalkyl-(C₁–C₄)-alkanediyl, (C₅–C₁₀)-aryl,
(C₅–C₁₀)-aryl-(C₁–C₄)-alkanediyl, it being possible
for the alkyl radicals to be substituted by 1–6 fluorine
atoms;

R⁹ is C(O)R¹⁰;

R¹⁰ is OH, (C₁–C₅)-alkoxy, (C₅–C₁₀)-aryl-(C₁–C₆)-
alkanediyloxy, (C₅–C₁₀)-aryloxy, (C₁–C₆)-
alkylcarbonyloxy-(C₁–C₄)-alkanediyloxy, (C₅–C₁₀)-
aryl-(C₁–C₄)-alkanediylcarbonyloxy-(C₁–C₄)-
alkanediyloxy, NH₂, mono- or di-(C₁–C₆-alkyl)-
amino;

R¹¹ is H, (C₁–C₆)-alkyl which is optionally mono- or
polysubstituted by fluorine, (C₃–C₆)-cycloalkyl,
(C₃–C₆)-cycloalkyl-(C₁–C₄)-alkanediyl, (C₅–C₁₀)-
aryl, (C₅–C₁₀)-aryl-(C₁–C₄)-alkanediyl, H₂N,
R⁸OR⁷, R⁸OC(O)R⁷, R⁸—(C₅–C₁₀)-arylene-R⁷,
R⁸R⁸NR⁷, R⁸NHC(O)R⁷, R⁸C(O)NHR⁷, H₂N—C
(=NH)—, H₂N—C(=NH)—NH—, =O;

n is 1 or 2;

q is 0 or 1;

in all their stereoisomeric forms and mixtures thereof in any
ratio; and their physiologically tolerable salts.

Very particularly preferred compounds of the formula I
are those in which:

A is a direct bond, (C₁–C₄)-alkanediyl, —NR²—C(O)—
NR²—, —NR²—C(O)O—, —NR²—S(O)ₙ—,
—NR²—S(O)ₙ—NR²—, —NR²—CO— or —NR²—,
which in each case can be mono- or disubstituted by
(C₁–C₄)-alkanediyl;

B is a direct bond or (C₁–C₄)-alkanediyl;

D is a direct bond, (C₁–C₄)-alkanediyl or —O—,
—NR²—, —NR²—CO—, —C(O)—NR²—, —NR²—
C(O)—NR²—, which in each case can be mono- or
disubstituted by (C₁–C₄)-alkanediyl;

E is phenylene or pyridinediyl which is optionally sub-
stituted by 1 or 2 radicals from the group consisting of
R², R³;

F is a direct bond, (C₁–C₆)-alkanediyl, or —O—,
—CO—NR²—, —NR²—CO—, —NR²—C(O)—

$NR^2$—, —$S(O)_2$—$NR^2$—, —$NR^2$—$S(O)_2$—, —$CR^2$=$CR^3$—, —C≡C—, which in each case can be mono- or disubstituted by ($C_1$–$C_4$)-alkanediyl;

G is

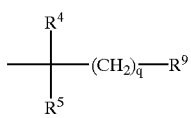

Y is a direct bond or —NH—;
$R^1$ is $R^2R^3N$—C(=$NR^2$)—,

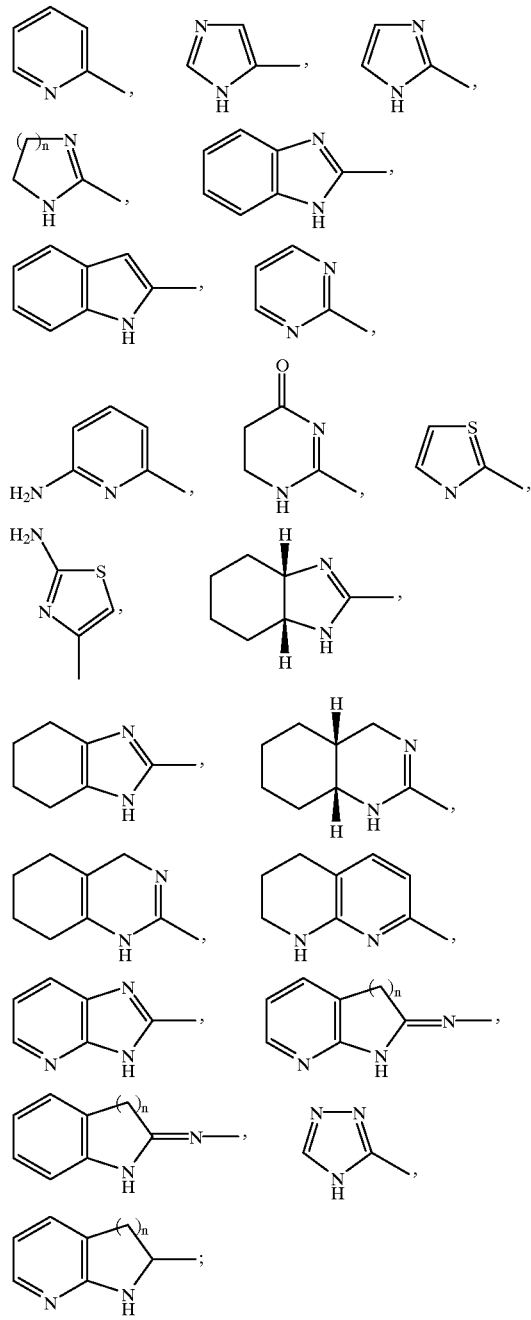

$R^2$, $R^3$ independently of one another are H, ($C_1$–$C_6$)-alkyl, trifluoromethyl, pentafluoroethyl, ($C_5$–$C_6$)-cycloalkyl, ($C_5$–$C_6$)-cycloalkyl-($C_1$–$C_2$)-alkanediyl, phenyl, benzyl, $H_2N$, $R^8OR^7$, $R^8R^8NR^7$, $R^8NHC(O)R^7$, $H_2N$—C(=NH)—, $H_2N$—C(=NH)—NH—;

$R^4$ is ($C_{10}$–$C_{12}$)-cycloalkyl, ($C_{10}$–$C_{12}$)-cycloalkyl-($C_1$–$C_6$)-alkanediyl, or $R^6OR^7$, $R^6R^8NR^7$, $R^6NHC(O)OR^7$, $R^6S(O)_nNHR^7$, $R^6OC(O)NHR^7$, $R^6C(O)NHR^7$, the cycloalkyl radicals preferably being 1-adamantyl or 2-adamantyl and the cycloalkylalkanediyl radicals preferably being adamantyl-1—($C_1$–$C_3$)-alkanediyl or adamantyl-2—($C_1$–$C_3$)-alkanediyl and it being possible for them to be substituted 1 or 2 times by ($C_1$–$C_4$)-alkyl, trifluoromethyl, phenyl, benzyl, ($C_1$–$C_4$)-alkoxy, phenoxy, benzyloxy, =O or mono- or di-($C_1$–$C_4$-alkyl)-amino, adamantyl radicals substituted 1 or 2 times as described above or ($C_{11}$–$C_{12}$)-cycloalkyl radicals which are unsubstituted or substituted 1 or 2 times as described above being particularly preferred;

$R^5$ is H, ($C_1$–$C_4$)-alkyl, trifluoromethyl;

$R^6$ is ($C_{10}$–$C_{12}$)-cycloalkyl, ($C_{10}$–$C_{12}$)-cycloalkyl-($C_1$–$C_6$)-alkanediyl, the cycloalkyl radicals preferably being 1-adamantyl or 2-adamantyl and the cycloalkylalkanediyl radicals preferably being adamantyl-1—($C_1$–$C_3$)-alkanediyl or adamantyl-2—($C_1$–$C_3$)-alkanediyl and it being possible for them to be substituted 1 or 2 times by ($C_1$–$C_4$)-alkyl, trifluoromethyl, phenyl, benzyl, ($C_1$–$C_4$)-alkoxy, phenoxy, benzytoxy, =O or mono- or di-($C_1$–$C_4$-alkyl)-amino, adamantyl radicals substituted 1 or 2 times as described above or ($C_{11}$–$C_{12}$)-cycloalkyl radicals which are unsubstituted or substituted 1 or 2 times as described above being particularly preferred;

$R^7$ is a direct bond or ($C_1$–$C_6$)-alkanediyl;

$R^8$ is H, ($C_1$–$C_6$)-alkyl, ($C_5$–$C_6$)-cycloalkyl, ($C_5$–$C_6$)-cycloalkyl-($C_1$–$C_2$)-alkanediyl, ($C_5$–$C_6$)-aryl, ($C_5$–$C_6$)-aryl-($C_1$–$C_2$)-alkanediyl;

$R^9$ is C(O)$R^{10}$;

$R^{10}$ is OH, ($C_1$–$C_6$)-alkoxy, phenoxy, benzyloxy, ($C_1$–$C_4$)-alkylcarbonyloxy-($C_1$–$C_4$)-alkanediyloxy, $NH_2$, mono- or di-($C_1$–$C_6$-alkyl)-amino;

n is 1 or 2;

q is 0 or 1;

in all their stereoisomeric forms and mixtures thereof in any ratio;

and their physiologically tolerable salts.

Especially preferred compounds of the formula I are those in which:

A is —NH—C(O)—;

B is ($C_1$–$C_4$)-alkanediyl;

D is —O—, —$NR^2$—C(O)—, —C(O)—$NR^2$— or a direct bond;

E is phenylene or pyridinediyl;

F is —$CH_2$— or —C(O)NH$CH_2$—;

G is

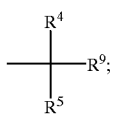

Y is a direct bond;
R$^1$ is H$_2$N—C(=NH)—,

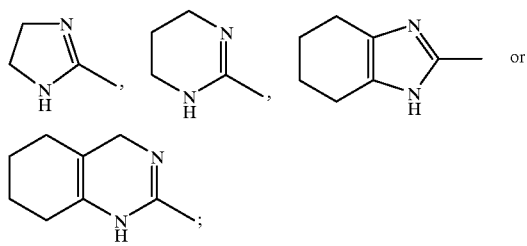

R$^2$ is H or (C$_1$–C$_4$)-alkyl;
R$^4$ is R$^6$OC(O)NH—;
R$^5$ is H;
R$^6$ is adamantyl-1—(C$_1$–C$_3$)-alkylene, adamantyl-2—(C$_1$–C$_3$)-alkylene, 1-adamantyl, 2-adamantyl, adamantyl preferably being substituted 1 or 2 times by (C$_1$–C$_4$)-alkyl, trifluoromethyl, phenyl, benzyl, (C$_1$–C$_4$)-alkoxy, phenoxy or benzyloxy, or (C$_{11}$–C$_{12}$)-cycloalkyl which can be substituted 1 or 2 times as above;
R$^9$ is C(O)R$^{10}$;
R$^{10}$ is OH, (C$_1$–C$_6$)-alkoxy, phenoxy, benzyloxy or (C$_1$–C$_4$)-alkoxycarbonyloxy-(C$_1$–C$_4$)-alkanediyloxy;
in all their stereoisomeric forms and mixtures thereof in any ratio;
and their physiologically tolerable salts.

Compounds of the formula I can generally be prepared, for example in the course of a convergent synthesis, by linkage of two or more fragments which can be derived retrosynthetically from the formula I. In the preparation of the compounds of the formula I, it may generally be necessary in the course of the synthesis temporarily to block functional groups which could lead to undesired reactions or side reactions in the respective synthesis step by means of a protective group strategy suited to the synthesis problem and known to the person skilled in the art using the present specification as a guide. The method of fragment coupling is not restricted to the following examples, but is generally applicable for syntheses of the compounds of the formula I.

For example, compounds of the formula I of the type

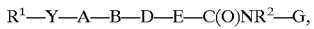
R$^1$—Y—A—B—D—E—C(O)NR$^2$—G, where F in the formula I is —C(O)NR$^2$— can be prepared by condensation of a compound of the formula II

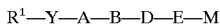
R$^1$—Y—A—B—D—E—M  II, where M is hydroxycarbonyl, (C$_1$–C$_6$)-alkoxycarbonyl, activated carboxylic acid derivatives such as acid chlorides, active esters or mixed anhydrides, with HNR$^2$—G. For the condensation of two fragments with formation of an amide bond, the coupling methods of peptide chemistry known per se (see, for example, Houben-Weyl, Methoden der Organischen Chemie [Methods of Organic Chemistry], Volume 15/1 and 15/2, Georg Thieme Verlag, Stuttgart, 1974) are advantageously used. For this purpose, as a rule it is necessary to protect nonreacting amino groups present during the condensation by reversible protective groups. The same applies to carboxyl groups not participating in the reaction, which are preferably employed as (C$_1$–C$_6$)-alkyl, benzyl or tert-butyl esters. Amino group protection is unnecessary if the amino groups to be generated are still present as nitro or cyano groups and are formed by hydrogenation only after coupling. After coupling, the protective groups present are removed in a suitable manner. For example, NO$_2$ groups (guanidino protection), benzyloxycarbonyl groups and benzyl esters can be removed by hydrogenation. The protective groups of the tert-butyl type are cleaved under acidic conditions, while the 9—fluorenylmethyloxycarbonyl radical is removed by secondary amines.

Compounds of the formula I in which R$^1$ has the meaning indicated, Y is —NR$^2$— and A is —C(O)— can be prepared, for example, by the generally known coupling methods of peptide chemistry by coupling R$^1$—NR$^2$H with HO$_2$C—B—D—E—F—G.

Compounds of the formula I where R$^9$=SO$_2$R$^{10}$ are prepared, for example, by oxidizing compounds of the formula I where R$^9$=SH by processes known from the literature (cf. Houben-Weyl, Methoden der Organischen Chemie [Methods of Organic Chemistry], Vol. E12/2, Georg Thieme Verlag, Stuttgart 1985, p. 1058 et seq.) to compounds of the formula I where R$^9$=SO$_3$H, from which the compounds of the formula I where R$^9$=SO$_2$R$^{10}$(R$^{10}$≠OH) are then prepared directly or via corresponding sulfonic acid halides by esterification or linkage of an amide bond. Oxidation-sensitive groups in the molecule, such as, for example, amino, amidino or guanidino groups are protected, if necessary, by suitable protective groups before carrying out the oxidation.

Compounds of the formula I where R$^9$=S(O)R$^{10}$ are prepared, for example, by converting compounds of the formula I where R$^9$=SH into the corresponding sulfide (R$^9$=S$^e$) and then oxidizing with meta-chloroperbenzoic acid to the sulfinic acids (R$^9$=SO$_2$H) (cf. Houben-Weyl, Methoden der Organischen Chemie [Methods of Organic Chemistry], Vol. E11/1. Georg Thieme Verlag, Stuttgart 1985, p. 618 et seq.), from which the corresponding sulfinic acid esters or amides R$^9$=S(O)R$^{10}$ (R$^{10}$≠OH) can be prepared by methods known from the literature. Generally, other methods known from the literature can also be used for the preparation of compounds of the formula I where R$^9$=S(O)$_n$R$^{10}$ (n=1, 2) (cf. Houben-Weyl, Methoden der Organischen Chemie [Methods of Organic Chemistry], Vol. E11/1, Georg Thieme Verlag, Stuttgart 1985, p. 618 et seq. or Vol. E11/2, Stuttgart 1985, p. 1055 et seq.).

Compounds of the formula I where R$^9$=P(O)(R$^{10}$)$_n$ (n=1, 2) are synthesized from suitable precursors by processes known from the literature (cf. Houben-Weyl, Methoden der Organischen Chemie [Methods of Organic Chemistry], Vol. E1 and E7, Georg Thieme Verlag, Stuttgart 1982), the synthesis method selected being suited to the target molecule.

Compounds of the formula I where R$^9$=C(S)R$^{10}$ can be prepared by processes known from the literature (cf. Houben-Weyl, Methoden der Organischen Chemie [Methods of Organic Chemistry], Vol. E5/1 and E5/2, Georg Thieme Verlag, Stuttgart 1985).

Compounds of the formula I where R$^9$=S(O)$_n$R$^{10}$ (n=1, 2), P(O)(R$^{10}$)$_n$ (n=1,2) or C(S)R$^{10}$ can of course also be prepared by fragment coupling, such as described above, which is advisable, for example, when, for example, a (commercially available) aminosulfonic acid, aminosulfinic acid, aminophosphonic acid or aminophosphinic acid or derivatives derived therefrom, such as esters or amides, are contained in F–G of the formula I.

Compounds of the formula I in which $R^1$—Y—A— is

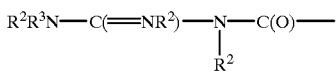

or cyclic acylguanidines of the type

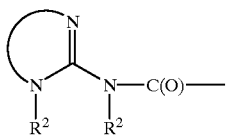

can be prepared, for example, by reacting a compound of the formula III $$Q(O)C\text{---}B\text{---}D\text{---}E\text{---}F\text{---}G \qquad \text{III}$$

in which Q is an easily nucleophilically substitutable leaving group, with the appropriate guanidine (derivative) of the type

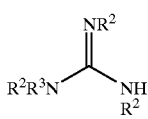

or the cyclic guanidine (derivative) of the type

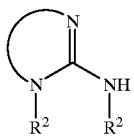

The activated acid derivatives of the formula III, in which Q is an alkoxy group, preferably a methoxy group, a phenoxy group, a phenylthio or methylthio 2—pyridylthio group, a nitrogen heterocycle, preferably 1-imidazolyl, are advantageously obtained in a manner known per se from the carboxylic acids (Q=OH) or carbonyl chlorides (Q=Cl) on which they are based. The latter are in turn obtained in a manner known per se from the carboxylic acids (Q=OH) on which they are based, for example by reaction with thionyl chloride.

Beside the carbonyl chlorides (Q=Cl), further activated acid derivatives of the type Q(O)C— can be prepared in a manner known per se directly from the carboxylic acids (Q=OH) on which they are based, such as, for example, the methyl esters (Q=OCH$_3$) by treating with gaseous HCl in methanol, the imidazolides (Q=1-imidazolyl) by treating with carbonyldiimidazole [cf. Staab, Angew. Chem. Int. Ed. Engl. 1, 351–367 (1962)], the mixed anhydrides (Q=C$_2$H$_5$OC(O)O or TosO) with Cl—COOC$_2$H$_5$ or tosyl chloride in the presence of triethylamine in an inert solvent. The activation of the carboxylic acids can also be carried out with dicyclohexylcarbodiimide (DCCI) or with O-[(cyano (ethoxy-carbonyl)methylene)amino]-1,1,3,3-tetramethyluronium tetrafluoroborate ("TOTU") [Weiss and Krommer, Chemiker Zeitung 98, 817 (1974)] and other activating reagents customary in peptide chemistry. A number of suitable methods for the preparation of activated carboxylic acid derivatives of the formula II are indicated stating source literature in J. March. Advanced Organic Chemistry, Third Edition (John Wiley & Sons, 1985), p. 350.

The reaction of an activated carboxylic acid derivative of the formula III with the respective guanidine (derivative) is carried out in a manner known per se in a protic or aprotic polar but inert organic solvent. In this context, methanol, isopropanol or THF from 20° C. up to the boiling temperature of these solvents have proven suitable in the reaction of the methyl esters (Q=OCH$_3$) with the respective guanidines. In the case of most reactions of compounds of the formula III with salt-free guanidines, the reaction is advantageously carried out in aprotic inert solvents such as THF, dimethoxyethane, dioxane. However, if a base (such as, for example, NaOH) is used, it is also possible to use water as a solvent in the reaction of compounds of the formula III with guanidines. If Q=Cl, the reaction is advantageously carried out with addition of an acid scavenger, e.g. in the form of excess guanidine (derivative) to bind the hydrohalic acid.

Compounds of the formula I in which $R^1$—Y—A— is $R^2$—C(=NR$^2$)—C(O)— or a system comprising a mono- or polycycle of the type

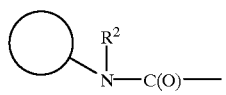

Compounds of the formula I in which $R^1$—Y—A is a sulfonyl- or sulfoxylguanidine of the type $R^2R^3N$—C(=NR$^2$)—NR$^2$—S(O)$_n$— (n =1, 2) or a sulfonyl- or sulfoxylaminoguanidine of the type $R^2R^3N$—C(=NR$^2$)—NR$^2$—NR$^2$—S(O)$_n$— (n=1, 2) or

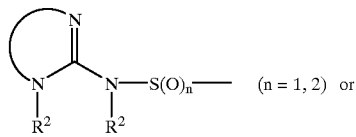

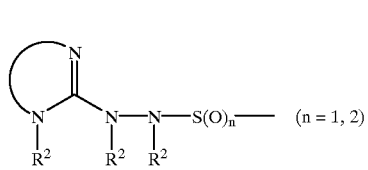

are prepared by processes known from the literature by reaction of $R^2R^3N$—C(=NR$^2$)—NR$^2$H or $R^2R^3N$—C(=NR$^2$)—NR$^2$—NR$^2$H or

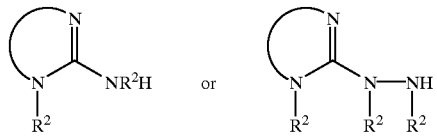

with sulfinic or sulfonic acid derivatives of the formula IV $$Q\text{---}S(O)_n\text{---}B\text{---}D\text{---}E\text{---}F\text{---}G \qquad \text{IV}$$

in which Q, for example, is Cl or NH$_2$, analogously to S. Birtwell et al., J. Chem. Soc. (1946) 491 or Houben-Weyl, Methoden der Organischen Chemie [Methods of Organic Chemistry], Vol. E4, Georg Thieme Verlag, Stuttgart 1983; p. 620 et seq.

Compounds of the formula I in which $R^1$—Y—A— is $R^2$—C(=NR$^2$)—NR$^2$—S(O)$_n$—(n=1, 2) or $R^2$—C (=NR²)—NR²—S(O)ₙ— (n=1, 2) or a system comprising a mono- or polycycle of the type

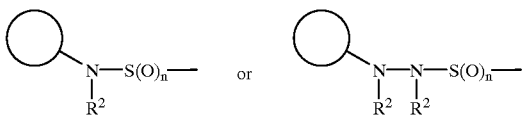

(n=1, 2) can be obtained analogously.

Compounds of the formula I in which Y has the meaning indicated, A is —NR²—C(O)—NR²—, —NR²—C(O)O—, —NR²—C(O)S— and R¹ is R²R³N—C(=NR²)—, R²—C(=NR²)— or a 4–10-membered mono- or polycyclic, aromatic or nonaromatic ring system which is specified as described above and can be substituted as described there, are prepared, for example, by reacting a compound of the formula V

   V in which Q is HNR²—, HO— or HS—, with a suitable carbonic acid derivative, preferably phosgene, diphosgene (trichloromethyl chloroformate), triphosgene (bistrichloromethyl carbonate), ethyl chloroformate, i-butyl chloroformate, bis(1-hydroxy-1-H-benzotriazolyl) carbonate or N,N'-carbonyldiimidazole, in a solvent which is inert to the reagents used, preferably DMF, THF or toluene, at a temperature between −20° C. and the boiling point of the solvent, preferably between 0° C. and 60° C. first to give a substituted carbonic acid derivative of the formula VI

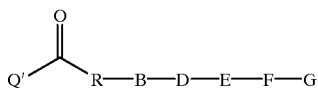   VI in which R is —NR²—, —O— or —S— and Q', depending on the carbonic acid derivative used, is chlorine, ethoxy, isobutoxy, benzotriazoi-1-oxy or 1-imidazolyl.

The reaction of these derivatives—in the case where Y is a direct bond—with R²R³N—C(=NR²)—NR²H or R²—C(=NR²)—NR²H or, if Y is —NR²—, with R²R³N—C(=NR²)—NR²—NR²H or R²—C(=NR²)—NR²—NR²H or with the systems comprising a mono- or polycycle of the type

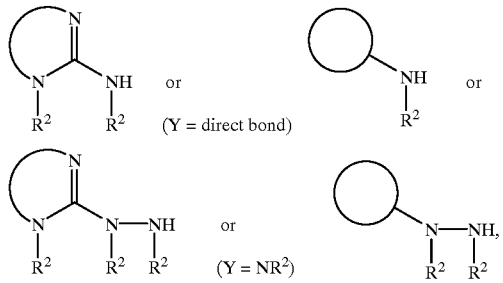

is carried out as described above in the preparation of acylguanidine (derivatives).

Compounds of the formula I in which F is —R²N—C(O)—NR²— or —R²N—C(S)—NR²— are prepared, for example, by reacting a compound of the formula VII

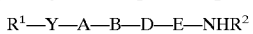   VII with an isocyanate OCN—G or isothiocyanate SCN—G by processes known from the literature.

Compounds of the formula I, in which F is —C(O)NR²—, —SO₂NR²— or —C(O)O— can be prepared, for example, by reaction of

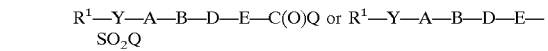

(Q is an easily nucleophilically substitutable leaving group, such as, for example, OH, Cl, OCH₃ etc.) with HR²N—G or HO—G by processes known from the literature.

Compounds of the formula I in which Y is a bond and R¹—A— comprises a mono- or polycycle of the type

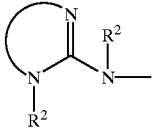

can be prepared, for example, by reacting a compound of the formula VIII

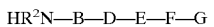   VIII with a mono- or polycycle of the type

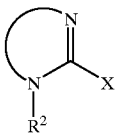

in which X is a nucleophilically substitutable leaving group such as, for example, halogen or SH, SCH₃, SOCH₃, SO₂CH₃ or HN—NO₂, by processes known from the literature (see, for example, A. F. Mckay et al., J. Med. Chem. 6 (1963) 587, M. N. Buchman et al., J. Am. Chem. Soc. 71 (1949), 766, F. Jung et al., J. Med. Chem. 34 (1991) 1110 or G. Sorba et al., Eur. J. Med. Chem. 21 (1986), 391).

Compounds of the formula I in which Y is a bond and R¹—A— comprises a mono- or polycycle of the type

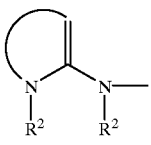

can be prepared, for example, by reacting a compound of the formula VIII with a compound of the type

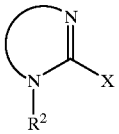

in which X is a leaving group, such as, for example —SCH₃, by processes known from the literature (cf., for example, T. Hiroki et al., Synthesis (1984) 703 or M. Purkayastha et al., Indian J. Chem. Sect. B 30 (1991) 646).

Compounds of the formula I in which D is —C≡C— can be prepared, for example, by reacting a compound of the formula IX

   IX in which X is I or Br with a compound of the type R¹—Y—A—B—C≡CH in a palladium-catalyzed reaction, such as described, for example, in A. Arcadi et al., Tetrahedron Lett. 1993, 34, 2813 or E. C. Taylor et al. J. Org. Chem. 1990, 55, 3222.

Analogously, compounds of the formula I in which F is —C≡C— can be prepared, for example, by linkage of compounds of the formula X

R¹—Y—A—B—D—E—X    X in which X is I or Br with a compound of the type HC≡C—G in a palladium-catalyzed reaction.

Preparation processes known from the literature are described, for example, in J. March, Advanced Organic Chemistry, Third Edition (John Wiley & Sons, 1985).

The compounds of the formula I according to the invention inhibit bone resorption by osteoclasts. Bone diseases against which the compounds according to the invention can be employed are especially osteoporosis, hypercalcemia, osteopenia, e.g. caused by metastases, dental disorders, hyperparathyroidism, periarticular erosions in rheumatoid arthritis and Paget's disease.

The compounds of the formula I can furthermore be employed for the alleviation, avoidance or therapy of bone disorders which are caused by a glucocorticoid, steroid or corticosteroid therapy or by a deficiency of sex hormone(s). All these disorders are characterized by bone loss, which is based on the inequilibrium between bone formation and bone destruction.

The compounds of the formula I can furthermore be used as carriers for active compounds in order to transfer the active compounds specifically to the site of action (=drug targeting, see, for example, Targeted Drug Delivery, R. C. Juliano, Handbook of Experimental Pharmacology Vol. 100, Ed. Born, G. V. R. et al., Springer Verlag). The active compounds are those which can be used for the treatment of the abovementioned diseases.

The compounds of the formula I and their physiologically tolerable salts can be administered to animals, preferably to mammals, and in particular to humans as medicaments by themselves, in mixtures with one another or in the form of pharmaceutical preparations which allow enteral or parenteral administration and which as an active constituent contain an efficaceous dose of at least one compound of the formula I or of a salt thereof, in addition to customary pharmaceutically innocuous excipients and additives. The preparations normally contain approximately 0.5 to 90% by weight of the therapeutically active compound.

The medicaments can be administered orally, e.g. in the form of pills, tablets, lacquered tablets, sugar-coated tablets, granules, hard and soft gelatin capsules, solutions, syrups, emulsions, suspensions or aerosol mixtures. Administration can also be carried out rectally, however, e.g. in the form of suppositories, or parenterally, e.g. in the form of injection or infusion solutions, microcapsules or rods, percutaneously, e.g. in the form of ointments or tinctures, or nasally, e.g. in the form of nasal sprays.

The pharmaceutical preparations are prepared in a manner known per se, pharmaceutically inert inorganic or organic excipients being used. For the production of pills, tablets, sugar-coated tablets and hard gelatin capsules, it is possible to use, for example, lactose, maize starch or derivatives thereof, talc, stearic acid or its salts etc. Excipients for soft gelatin capsules and suppositories are, for example, fats, waxes, semisolid and liquid polyols, natural or hardened oils, etc. Suitable excipients for the preparation of solutions and syrups are, for example, water, sucrose, invert sugar, glucose, polyols, etc. Suitable excipients for the production of injection solutions are water, alcohols, glycerol, polyols, vegetable oils, etc. Suitable excipients for microcapsules, implants or rods are copolymers of glycolic acid and lactic acid.

Beside the active compounds and excipients, the pharmaceutical preparations can also contain additives, such as, for example, fillers, extenders, disintegrants, binders, lubricants, wetting agents, stabilizers, emulsifiers, preservatives, sweeteners, colorants, flavorings or aromatizers, thickening agents, diluents, buffer substances, furthermore solvents or solubilizers or agents for achieving a depot effect, and salts for altering the osmotic pressure, coating agents or antioxidants. They can also contain two or more compounds of the formula I or their physiologically tolerable salts; furthermore beside at least one compound of the formula I, also one or more other therapeutically active substances.

The dose can vary within wide limits and is to be suited to the individual conditions in each individual case. In the case of oral administration, the daily dose is in general from 0.01 to 50 mg/kg, preferably 0.1 to 5 mg/kg, in particular 0.3 to 0.5 mg/kg, of bodyweight to achieve efficacious results; in the case of intravenous administration the daily dose is in general approximately 0.01 to 100 mg/kg, preferably 0.05 to 10 mg/kg, of body weight. In particular in the case of the administration of relatively large amounts, the daily dose can be divided into more than one, e.g. 2, 3 or 4, part administrations. In some cases it may be necessary, depending on individual behavior, to deviate upward or downward from the daily dose indicated.

The present invention will now be further described by reference to the following non-limiting examples.

EXAMPLES

The products were identified by means of mass spectra and/or NMR spectra.

Example 1

(2S)-2-(1-Adamantyl-methyloxycarbonylamino)-3-(4-(3-guanidinocarbonyl-propyloxy)phenyl) propionic Acid (1.5)

The synthesis was carried out according to the following reaction sequence:

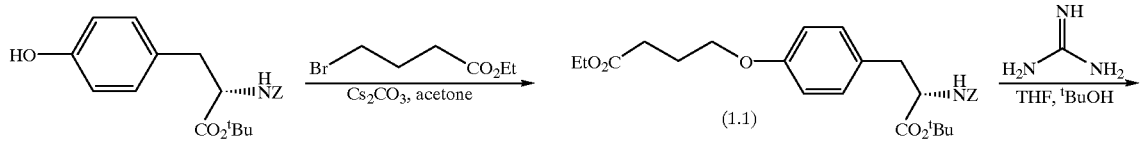

-continued

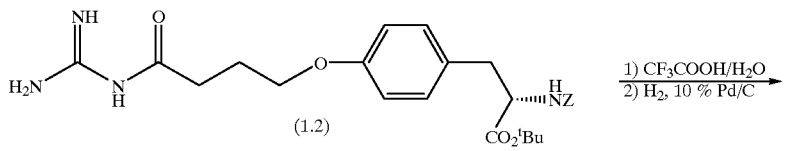

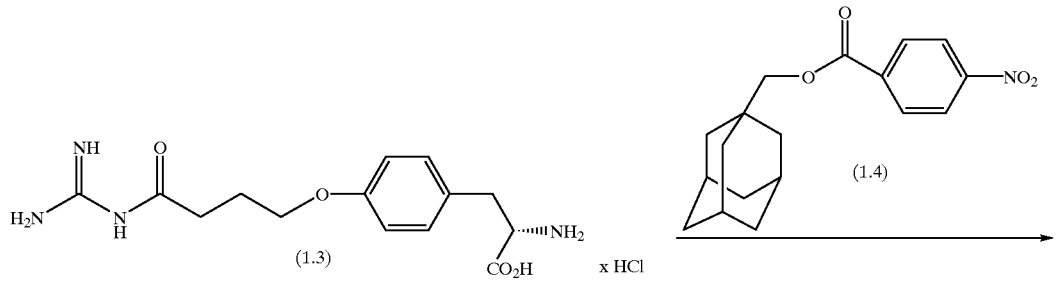

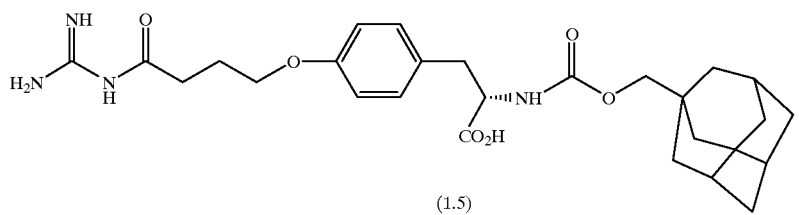

1a) tert-Butyl (2S)-2-benzyloxycarbonylamino-3-(4-(3-ethoxycarbonyl-propyloxy)phenyl)propionate (1.1)

8.29 ml (57.9 mmol) of ethyl 4-bromobutanoate and 28.21 g (86.58 mmol) of cesium carbonate were added to 21.5 g (57.9 mmol) of tert-butyl N-benzyloxycarbonyltyrosine in 280 ml of acetone and the mixture was heated to reflux with stirring. After 2 h, a further 2 ml of ethyl 4-bromobutanoate and 2 g of cesium carbonate were added, after a further 2 h a further 2 ml of ethyl 4-bromobutanoate and 3 g of cesium carbonate were added and after standing at room temperature overnight 9 ml of ethyl 4-bromobutanoate were added again and the mixture was heated to reflux for a further 6 h. After cooling, it was filtered, the residue was washed with acetone and the filtrate was concentrated. The residue was taken up in diethyl ether and the organic phase was washed successively with 3% strength citric acid solution, 3×H$_2$0 and saturated NaCl solution. The ether phase was dried over MgSO$_4$, the drying agent was filtered off and the filtrate was concentrated in vacua. The residue was chromatographed on silica gel using CH$_2$Cl$_2$ and CH$_2$Cl$_2$MeOH (99/1). 31.3 g of a pale yellow oil were obtained, which was employed without further purification for the synthesis of (1.2).

1b) tert-Butyl (2S)-2-benzyloxycarbonylamino-3-(4-(3-guanidinocarbonyl-propyloxy)phenyl)propionate (1.2)

A solution of 3.64 g (61.69 mmol) of guanidine in 150 ml of tert-butanol was added to a solution of 20 g (41.23 mmol) of (1.1) in THF and the mixture was stirred at room temperature for 18 h. A further 4.5 g of guanidine in 150 ml of tert-butanol were then added, and the reaction solution was stirred at room temperature for 7 h, concentrated to about a half and stirred at room temperature for a further 18 h. The solvent was removed in vacuo and the residue was first filtered through basic Al$_2$O$_3$ using CH$_2$Cl$_2$/MeOH/H$_2$O (95/5/0.5) and then chromatographed on silica gel by means of MPLC using CH$_2$Cl$_2$/MeOH/acetic acid (90/10/0.5). 8.6 g (42%) of (1.2) were obtained.

1c) (2S)-2-Amino-3-(4-(3-guanidinocarbonylpropyloxy)phenyl)propionic acid hydrochloride (1.3)

30 ml of 95% strength trifluoroacetic acid were added to 8.6 g (17.3 mmol) of (1.2) and the mixture was stirred at room temperature for 25 min. The reaction mixture was concentrated in a rotary evaporator and then concentrated twice with toluene. The residue was taken up in dilute acetic acid, treated with water and freeze-dried. The colorless solid thus obtained was purified on silica gel by means of MPLC using CH$_2$Cl$_2$/MeOH/acetic acid (90/10/0.5). After concentrating and freeze-drying, 5.5 g (72%) of a colorless solid were obtained.

400 mg of this substance were dissolved in 30 ml of MeOH and after addition of methanolic hydrogen chloride solution the benzyloxycarbonyl protective group was cleaved hydrogenolytically over 10% Pd/C. The precipitated product was dissolved by addition of DMF, the catalyst was filtered off, the filtrate was concentrated and the residue was freezedried. 320 mg of (1.3) were obtained as a colorless solid.

1d) 1-Adamantylmethyl 4-nitrophenylcarbonate (1.4)

605 mg (3 mmol) of 4-nitrophenyl chlorofornate were added to a solution of 499 mg (3 mmol) of 1-hydroxymethyladamantane in 7 ml of pyridine and the mixture was stirred overnight at room temperature. After concentrating in a high vacuum, the residue was employed directly for the preparation of (1.5).

1e) (2S)-2-(1-Adamantylmethyloxycarbonylamino)-3-(4-(3-guanidinocarbonylpropytoxy)phenyl)propionic acid (1.5)

114.5 mg of (1.4) were added to a solution of 146 mg (0.35 mmol) of (1.3) in 2 ml of DMF and the mixture was stirred overnight at room temperature. 0.059 ml of diisopropylethylamine was added and the mixture was again stirred overnight at room temperature. After removing the solvent in vacuo, the residue was partitioned between ethyl acetate and water. The organic phase was dried over $MgSO_4$,  concentrated and then treated with diisopropyl ether. The precipitate was filtered off and purified by means of preparative thin-layer chromatography using $CH_2Cl_2$/MeOH/acetic acid (100/25/2). 10 mg of (1.5) were obtained.

Example 2

(2S)-2-((2-(1-Adamantyl)ethyl)oxycarbonylamino)-3-(4-(3guanidinocarbonyl-propyloxy)phenyl) propionic Acid (2.2)

The synthesis was carried out according to the following reaction sequence:

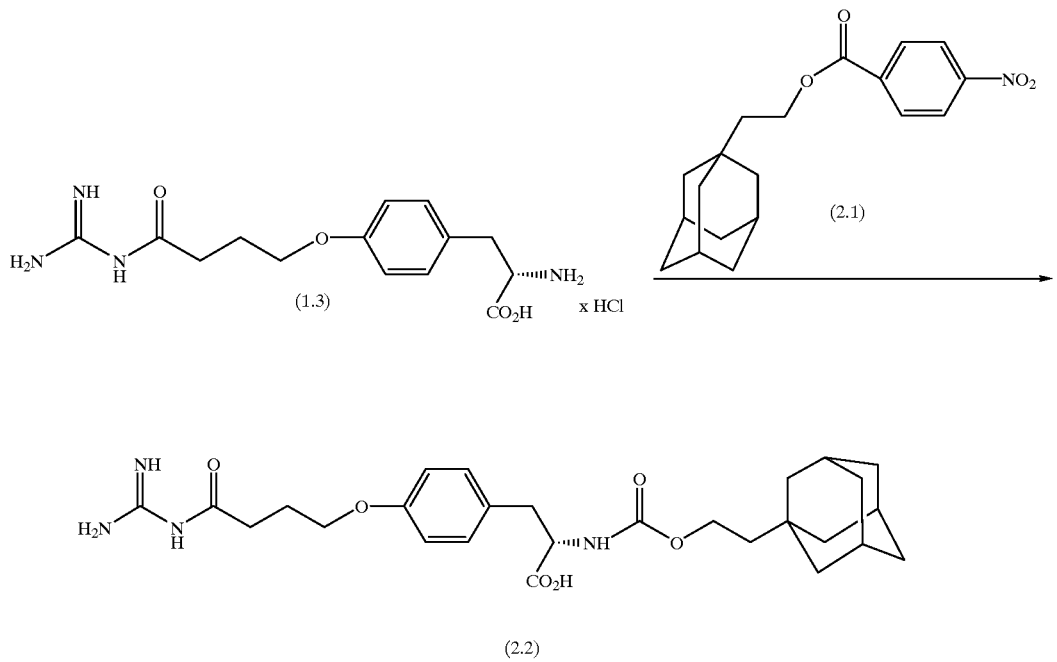

The synthesis of (1.3) was carried out as described in Example 1 c). Compound (2.1) was prepared from 1-(2-hydroxyethyl)adamantane and 4-nitrophenyl chloroformate analogously to the synthesis of compound (1.4) (Example 1d) and employed directly for the synthesis of (2.2).

(2S)-2-((2-(1-Adamantyl)ethyl)oxycarbonylamino)-3-(4-(3-guanidinocarbonyl-propyloxy)phenyl) propionic Acid (2.2)

119 mg of (2.1) were added to a solution of 146 mg (0.35 mmol) of (1.3) in 2 ml of DMF and the mixture was stirred overnight at room temperature. 2.3 mg of imidazole and 0.3 ml of pyridine were added and the mixture was again stirred overnight at room temperature. The solution was concentrated, the residue was partitioned between water and ethyl acetate, the organic phase was dried over $MgSO_4$ and, after filtration, the solvent was removed in vacuo. The residue was separated by means of preparative thin-layer chromatography using $CH_2Cl_2$/MeOH/acetic acid (100/25/2). 19 mg of (2.2) were obtained.

Example 3

(2S)-2-(1-Adamantylmethyfoxycarbonylamino)-3-(4-(2-(1,4,5,6-tetrahydropyrimidin-2-ylcarbamoyl) ethyl)benzoylamino)propionic Acid (g)

The synthesis was carried out according to the following reaction sequence

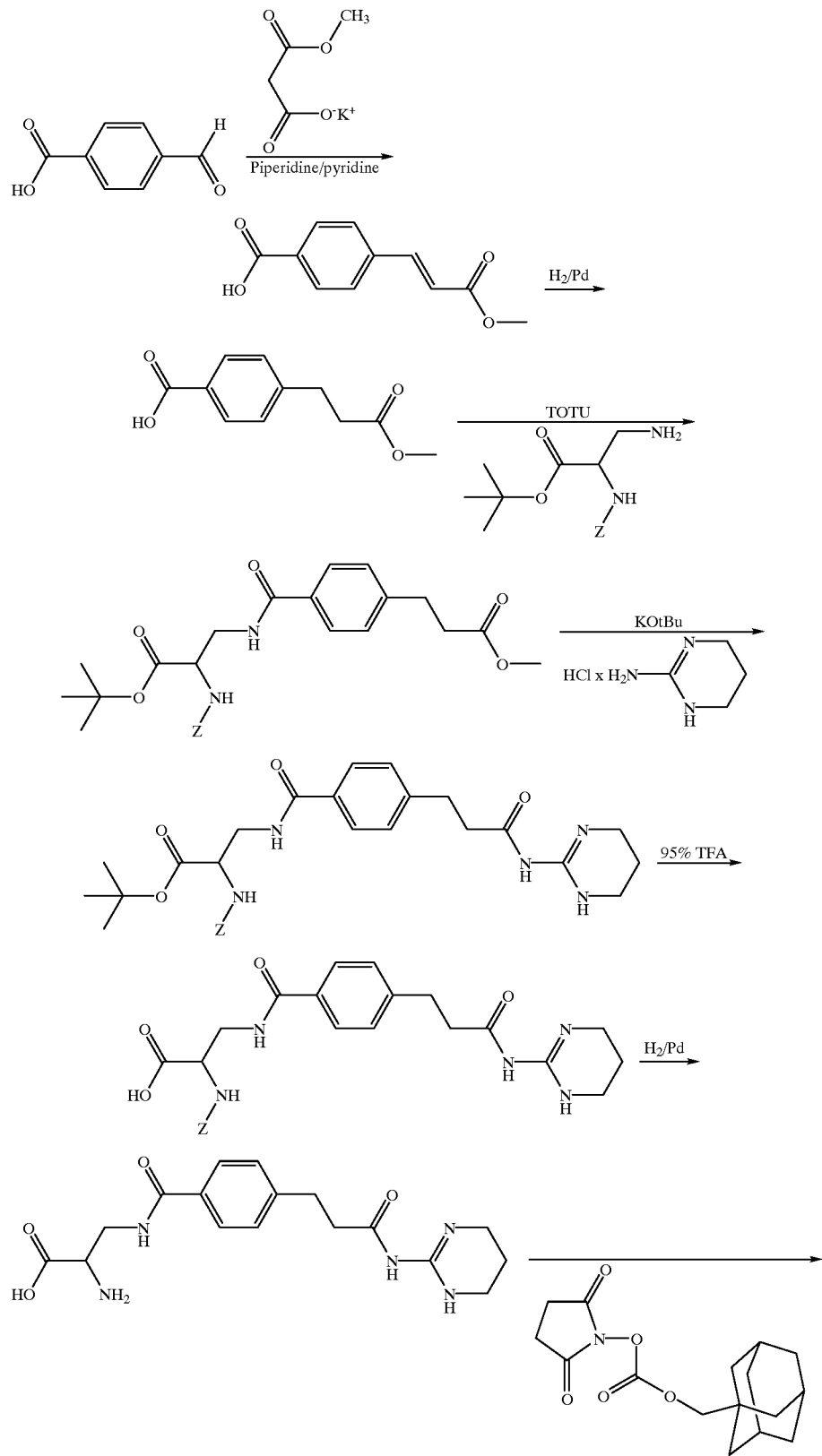

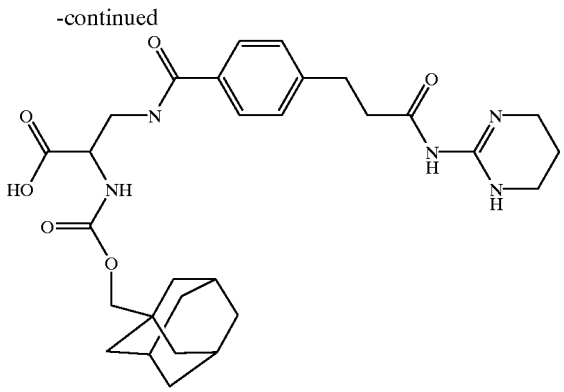

3a) 4-(2-Methoxycarbonylvinyl)benzoic acid 18.74 g (0.12 mol) of potassium monomethyl malonate were suspended in 18 ml of pyridine. 15.01 g (0.1 mol) of 4-carboxybenzaldehyde and 0.85 g (0.01 mol) of piperidine were added at room temperature (RT) with stirring and the mixture was boiled under reflux until the evolution of $CO_2$ had ended (about 2 h). A further 60 ml of pyridine were added and the mixture was stirred under reflux for a further 1 h. The reaction mixture was treated with stirring with 500 ml of ice and 110 ml of conc. HCl. After addition was complete, the mixture was stirred for a further 20 min, and the product was filtered off with suction, washed with water and recrystallized from isopropanol. Yield: 12.85 g (62%).

$^1$H NMR (200 MHz, DMSO): δ=3.75 (s, 3H, OCH$_3$); 6.76 (d, J=15 Hz, 1H, CHCOOCH$_3$); 7.73 (d, J=15 Hz, 1 H, Ar—CH); 7.84 (d, J =9 Hz, 2H, Ar—H); 7.98 (d, J =9 Hz, 2H, Ar—H); 13.11 (s, broad, 1H, COOH) MS: Cl$^+$, m/e=207.2 (M+H$^+$, 100%) HPLC: (RP18: Nucleosil 300-5-C18, 250×4 mm), buffer A: H$_2$O, 0.1% TFA; buffer B: acetonitrile (80% v/v); H$_2$O (20% v/v); 0.1% TFA; gradient: (1) 5 min, 10% buffer B; (2) over 20 min to 90% buffer B; (3) 5 min 90% buffer B; flow rate 1 ml/min; R$_t$=18.05 min.

3b) 4-(2-Methoxycarbonylethyl)benzoic acid 8 g (38.8 mmol) of 4-(2-methoxycarbonylvinyl)benzoic acid (Example 3a) were suspended in 250 ml of dioxane and hydrogenated with 1 bar H$^2$ over Pd/C (10%) at RT for 7 h. The mixture was filtered and the solvent was evaporated in vacuo. Yield: 8.05 g (100%).

$^1$H NMR (200 MHz, DMSO): d=2.67 (t, J=8 Hz, 2H, CH$_2$—COOMe); 2.93 (t, J=8 Hz, 2H, Ar—CH$_2$); 3.59 (s, 3H, OCH$_3$); 7.35 (d, 2H, Ar—H); 7.86 (d, J=9 Hz, 2H, Ar—CH$_2$; 12.80 (s, broad, 1H, COOH); MS: Cl$^+$, m/e= 209.2 (M+H$^+$, 100%); HPLC: (RP18: Nucleosil 300-5-C18, 250×4 mm), buffer A: H$_2$O, 0.1% TFA; buffer B: acetonitrile (80% v/v); H$_2$O (20% v/v); 0.1% TFA; gradient: (1) 5 min, 10% buffer B; (2) over 20 min to 90% buffer B; (3) 5 min 90% buffer B; flow rate 1 ml/min; R$_t$=17.03 min.

3c) tert-Butyl (2S)-2-benzyloxycarbonylamino-3-(4-(2-methoxycarbonyl-ethyl)benzoylamino)propionate 354 mg (1.7 mmol) of 4-(2-methoxycarbonylethyl) benzoic acid (Example 3b) and 500 mg (1.7 mmol) of tert-butyl (2S)-2-benzyloxycarbonylaminno-3-amino-propionate were dissolved in 3 ml of DMF and treated with 557 mg (1.7 mmol) of O-[(cyano(ethoxycarbonyl) methylidene)amino]-1,1,3,3, -tetramethyluronium tetrafluo-roborate (TOTU) and 204 mg (1.7 mmol) of diisopropyl-ethylamine (DIPEA) and the solution was stirred at RT for 7 h. The solvent was evaporated in vacuo, the residue was dissolved in ethyl acetate (EA) and washed three times each with KHSO$_4$ and NaHCO$_3$ solution until neutral, the organic phase was separated off and dried, and the solvent was distilled off in vacuo. Yield: 770 mg (93%). MS: ES$^+$, m/e=485.2 (M+H$^+$, 100%)

3d) tert-Butyl (2S)-2-benzyloxycarbonylamino-3-(4-(2-(1,4, 5,6-tetrahydro-pyrimidin-2-ylcarbamoyl)ethyl) benzoylamino)propionate 1.25 g (9.2 mmol) of 2-amino-1,4,5,6-tetrahydropyrimidine hydrochloride and 1.03 g (9.2 mmol) of potassium tert-butoxide were dissolved in 3 ml of absol. DMF and the mixture was stirred at RT for 30 min. 740 mg (1.53 mmol) of tert-butyl (2S)-2-benzyioxycarbonylamino-3-(4-(2-methoxycarbonylethyl)benzoylamino)propionate (Example 3c) in 1 ml of DMF were then added and the mixture was stirred at RT for 4h. It was adjusted to pH 4 using glacial acetic acid, the solvent was stripped off in vacuo, and the residue was chromatographed on silica gel (dichloromethane/methanol/glacial acetic acid/water (9/110.1/0.1)).

Yield: 190 mg (38%); MS: ES$^+$, m/e=552.3 (M+H$^+$, 100%).

3e) (2S)-2-Benzyloxycarbonylamino-3-(4-(2-(1,4,5,6-tetrahydropyrimidin-2—ylcarbamoyl)ethyl) benzoylamino)propionic acid 190 mg (0.34 mmol) of tert-butyl 2S-benzyloxycarbonylamino-3-(4-(2-(1,4,5,6-tetrahydropyrimidin-2-ylcarbamoyl)ethyl)benzoylamino) propionate (Example 3d) were dissolved in 5 ml of 95% trifluoroacetic acid and the mixture was stirred at RT for 1 h. The trifluoroacetic acid was distilled off in vacuo, the mixture was coevaporated with toluene, the residue was dissolved in glacial acetic acid, and the solution was diluted with water and freeze-dried.

Yield: 170 mg (100%); MS: ES$^+$, m/e=496.3 (M+H$^+$, 100%).

3f) (2S)-2-Amino-3-(4-(2-(1,4,5,6-tetrahydropyrimidin-2-ylcarbamoyl)-ethyl)benzoylamino)propionic acid 100 mg (0.2 mmol) of (2S)-2-benzyloxycarbonylamino-3-(4-(2-(1,4,5,6-tetra-hydropyrimidin-2-ylcarbamoyl)ethyl) benzoylamino)propionic acid (Example 3e) were dissolved in 15 ml of dioxane, treated with 0.012 ml of glacial acetic acid and hydrogenated at RT and 1 bar H$_2$ over Pd/C (5%). After 2 h, 15 ml of methanol were added and the mixture was hydrogenated at RT and 1 bar H$_2$ for a further 5 h. It was filtered and the solvent was evaporated in vacuo. Yield: 67.4 mg (93%).

MS: ES$^+$, m/e=362.2 (M+H$^+$, 30%); 173.0 (100).

3g) (2S)-2-(1-Adamantylmethyloxycarbonylamino)-3-(4-(2-(1,4,5,6-tetra-hydropyrimidin-2-ylcarbamoyl)ethyl) benzoylamino)propionic acid 67.4 mg (0.186 mmol) of 2S-amino-3-(4-(2-(1,4,5,6-tetrahydropyrimidin-2-ylcarbamoyl)ethyl)benzoylamino)

propionic acid (Example 3f were dissolved in 4 ml of dioxane. With stirring, first 4 ml of saturated NaHCO$_3$ solution, then 57 mg of 1-adamantylmethyl 2.5dioxopyrrolidin-1-yl carbonate were added at RT. The mixture was stirred at RT for 24 h and adjusted to pH 4 using glacial acetic acid, the solvent was stripped off in vacuo and the residue was chromatographed (20% (v/v) acetonitrile in water, 0.1% trifluoroacetic acid, up to 40% (v/v) acetonitrile) on RP-18 (Lichrospher C-18). Yield: 30 mg (30%).

MS: ES$^+$, m/e=554.4 (M+H$^+$, 100%).

Example 4
(2S)-2-(1-Adamantylmethyloxycarbonylamino)-3-(4-(3-(1,4,5,6-tetrahydropyrimidin-2-yl-carbamoyl)propyloxy)phenyl)propionic Acid

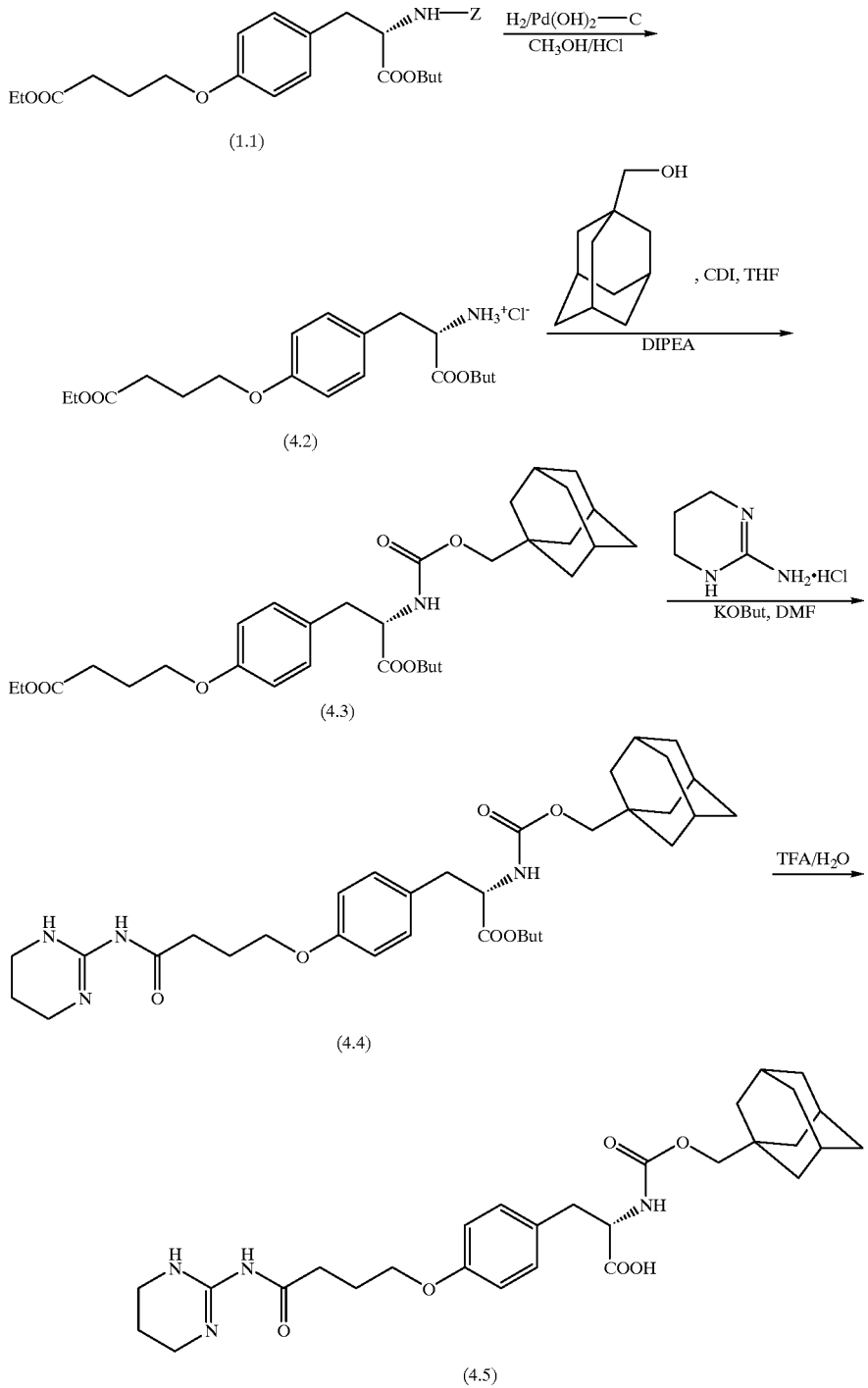

4a) tert-Butyl (2S)-2-amino-3-(4-(3-ethoxycarbonylpropyloxy)phenyl)propionate (4.2)

100 g (0.206 mol) of tert-butyl (2S)-2-benzyloxycarbonylamino-3-(4-(3-ethoxycarbonylpropyloxy)phenyl)propionate (1.1) from Example 1 were dissolved in 1 liter of methanol, the solution was treated with methanolic hydrogen chloride solution and with 10 g of 20% palladium hydroxide/carbon and hydrogen was passed in for 6 hours. Then the catalyst was filtered off, the solution was evaporated and the residue was treated with tert-butylether. The precipitate formed was filtered off. 72 g (90%) of an amorphous powder were obtained.

4b) tert-Butyl (2S)-2-(1-adamantylmethyloxycarbonylamino)-3-(4-(3-ethoxycarbonylpropyloxy)phenyl)propionate (4.3)

892 mg (5.5 mmol) of carbonyldiimidazole (CDI) were added to a solution of 830 mg (5 mmol) of 1-hydroxymethyladamantane in 10 ml of tetrahydrofuran and the mixture was stirred overnight at RT. it was then treated with 1 g (2.57 mmol) of tert-butyl (2S)-2-amino-3-(4-(3-ethoxycarbonyl-propyloxy)phenyl)propionate and 442 µl (2.57 mmol) of diisopropylethylamine (DIPEA) and the mixture was stirred overnight at 50° C. After cooling, it was taken up in ethyl acetate and the organic phase was washed successively with 3% strength citric acid solution, sodium hydrogencarbonate solution, 3×H$_2$O and saturated NaCl solution. The organic phase was dried using MgSO$_4$, the drying agent was filtered off and the filtrate was concentrated. The residue was chromatographed on silica gel using CH$_2$Cl$_2$/CH$_3$OH (99/1). 1.19 g (85%) of an oil were obtained, which was employed without further purification for the synthesis of (4.4).

4c) tert-Butyl (2S)-2-(1-adamantylmethyloxycarbonylamino)-3-(4-(3-(1,4,5,6-tetra-hydropyrimidin-2-ylcarbamoyl)propoxy)phenyl)propionate (4.4)

398 mg (2.94 mmol) of 2-amino-1,4,5,6-tetrahydropyrimidine hydrochloride were dissolved in 7 ml of methanol and treated with 330 mg (2.94 mmol) of potassium tert-butoxide. After 40 min, the precipitated salts were filtered off and the filtrate was concentrated. The residue was dissolved in 3 ml of dimethylformamide and added to a solution of 365 mg of tert-butyl (2S)-2-(1-adamantylmethyloxycarbonylamino)-3-(4-(3-ethoxycarbonylpropyloxy)-phenyl)propionate (4.3). The mixture was warmed at 40° C. for 5 hours, the solvent was removed in vacuo, the residue was taken up in ethyl acetate and the organic phase was washed 3× with H$_2$O and saturated sodium chloride solution. The organic phase was concentrated and the residue was chromatographed on silica gel using CH$_2$Cl$_2$/CH$_3$OH/ethyl acetate/H$_2$O (90:10:0.5:0.5). 100 mg of an amorphous powder were obtained. which was employed without further purification for the synthesis of (4.5).

4d) (2S)-2-(1-Adamantylmethyloxycarbonylamino)-3-(4-(3-(1,4,5,6-tetra-hydropyrimidin-2-ylcarbamoyl)propyloxy)phenylpropionic acid (4.5)

100 mg of the tert-butyl ester of Example 4.4 were dissolved in 10 ml of trifluoroacetic acid/H$_2$O (95:5). After 30 min, the reaction solution was concentrated and the residue was digested with diisopropyl ether. By subsequent freeze-drying, 85 mg of (4.5) were obtained.

Example 5

(2S)-2-(1-Adamantylmethyloxycarbonylamino)-3-(4-(3-(4,5-dihydroimidazol-2-ylcarbamoyl)propyloxy)phenyl)propionic Acid (5.2)

(5.2)

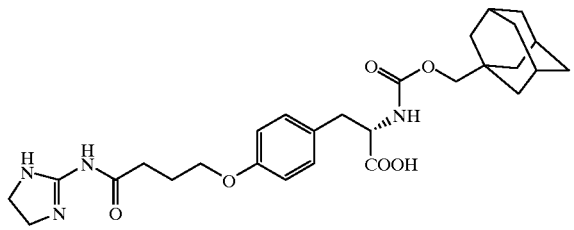

The synthesis was carried out analogously to Example 4.

5a) tert-Butyl (2S)-2-(1-adamantylmethyloxycarbonylamino)-3-(4-(3-(4,5-dihydroimidazoi-2-ylcarbamoyl)propyloxy)phenyl)propionate (5.1)

436 mg (0.8 mmol) of tert-butyl (2S)-2-(1-adamantylmethyloxycarbonylamino)-3-(4-(3-ethoxycarbonylpropyloxy)phenyl)propionate were added to a solution of 388 mg (3.2 mmol) of 2-amino4,5-dihydroimidazole hydrochloride and 359 mg (3.2 mmol) of potassium tert-butoxide in 10 ml of DMF. The mixture was stirred overnight. After the reaction had ended, it was worked up analogously to Example 4c and chromatographed on silica gel using the same eluent mixture. 188 mg (0.32 mmol) of (5.1) were obtained.

5b) (2S)-2-(1-Adamantylmethyloxycarbonylamino)-3-(4-(3-(4,5-dihydroimidazol-2-ylcarbamoyl)propyloxy)phenyl)propionic acid (5.2)

188 mg (0.32 mmol) of (5.1) were dissolved in 10 ml of trifluoroacetic acid/H$_2$O (95:5). After 30 min, the solvent was removed in vacuo and the residue was digested with diisopropyl ether. After freeze-drying, 168 mg of an amorphous powder of (5.2) were obtained.

Pharmacological Testing

The inhibition of bone resorption by the compounds according to the invention can be determined, for example, with the aid of an osteoclast resorption test ("PIT ASSAY"), for example analogously to WO 95/32710.

The inhibitory action of the compounds according to the invention against the vitronectin receptor $\alpha\beta_3$ can be determined, for example, as described below:

Test for the measurement of the inhibition of the binding of 293 cells to human vitronectin (abbreviated in the test results to Vn/293 cell test)

1. Purification of Human Vitronectin

Human vitronectin was isolated from human plasma and purified by affinity chromatography according to the method of Yatohyo et al., Cell Structure and Function, 1988, 23, 281–292.

2. Cell Test 293 cells, a human embryonic kidney cell line, which were cotransfected with DNA sequences for the $\alpha_V$ and $\beta_3$ subunits of the vitronectin receptor were selected according to the FACS method with a view to a high expression rate (>500,000 $\alpha_V\beta_3$ receptors/cell). The selected cells were cultured and sorted again by means of FACS to obtain a stable cell line (15 D) with expression rates of >1,000,000 copies of $\alpha_V\beta_3$ per cell.

A Linbro 96-well tissue culture plate with a flat bottom was coated overnight at 4° C. with human vitronectin (0.01 mg/ml, 0.05 ml/well) in phosphate-buffered saline solution (PBS) and then blocked with 0.5% strength BSA. Solutions of the test substances from $10^{-10}$–$2\times10^{-3}$ mol/l in glucose-containing DMEM medium were prepared and in each case 0.05 ml/well of the solution was added to the plates. The cells which exhibited high levels of $\alpha_V\beta_3$ (e.g. 15 D) were suspended in glucose-containing DMEM medium and the suspension was adjusted to a content of 25,000 cells/0.05 ml of medium. 0.05 ml of this cell suspension was added to each well and the plate was incubated at 37° C. for 90 min. The plate was washed 3× with warm PBS to remove unbound cells. The bound cells were lyzed in citrate buffer (25 mmol, pH 5.0), which contained 0.25% Triton X-100. The hexose amidase substrate p-nitrophenyl-N-acetyl-β-glucosaminide was then added and the plate was incubated at 37° C. for 90 min. The reaction was stopped with a glycine (50 mmol)/EDTA (5 mmol) buffer (pH 10.4) and the absorption of each well was measured at 405–650 nm. The data were evaluated using standard methods.

The following test results were obtained.

Vn/293 Cell test

IC$_{50}$ (μM)

| Compound of example 1 | 0.032 |
|---|---|
| Compound of example 3 | 0.032 |

Other embodiments of the invention will be apparent to those skilled in the art from consideration of the specification and practice of the invention disclosed herein. It is intended that the specification be considered as exemplary only, with the true scope and spirit of the invention being indicated by the following claims.

All references referred to herein are expressly incorporated by reference in their entireties.

Priority application Federal Republic of Germany No. 19629816.4 filed on Jul. 24. 1996 including the title, specification, claims and abstract, is hereby incorporated by reference.

What is claimed is:

1. A compound of formula (I),

R$^1$—Y—A—B—D—E—F—G    (I), in which:
A is a direct bond, (C$_1$–C$_6$)-alkanediyl, —NR$^2$—C(O)—NR$^2$—, —NR$^2$—C(O)O—, —NR$^2$—S(O)$_n$—NR$^2$—, —NR$^2$—S(O)$_n$—, (C$_3$–C$_6$)-cycloalkanediyl, —C≡C—, —NR$^2$—C(O)—, —C(O)—NR$^2$—, —O—, —CO—, —NR$^2$—, —CO$_2$—, or —CR$^2$=CR$^3$—, which in each case can be mono- or disubstituted by (C$_1$–C$_8$)-alkanediyl;

B is a direct bond, (C$_1$–C$_6$)-alkanediyl, or —CR$^2$=CR$^3$—, which can be mono- or disubstituted by (C$_1$–C$_6$)-alkanediyl;

D is a direct bond, (C$_1$–C$_6$)-alkanediyl, —O—, —NR$^2$—, —NR$^2$—CO—, —C(O)NR$^2$—, —NR$^2$—C(O)—NR$^2$—, —OC(O)—, —C(O)—, —S(O)$_2$—NR$^2$—, —NR$^2$—S(O)$_2$—, or —NR$^2$—S(O)$_2$—, which in each case can be mono- or disubstituted by (C$_1$–C$_6$)-alkanediyl;

E is phenylene or pyridinediyl which is optionally substituted by 1–3 identical or different radicals selected from the group consisting of R$^2$ and R$^3$;

F is a direct bond, (C$_1$–C$_6$)-alkanediyl, —O—, —CO—NR$^2$—, —NR$^2$—CO—, —NR$^2$—C(O)—NR$^2$—, —OC(O)—, —C(O)O—, —CO—, —S(O)$_2$—, —S(O)$_2$—NR$^2$—, —NR$^2$—S(O)$_2$—, —CR$^2$=CR$^3$—, or —C≡C—, which in each case can be mono- or disubstituted by (C$_1$–C$_6$)-alkanediyl;

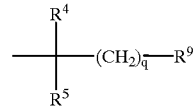

Y is a direct bond or —NH—;
R$^1$ is

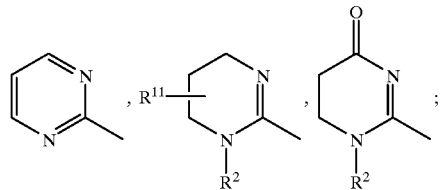

R$^2$, R$^3$ independently of one another are H, (C$_1$–C$_6$)-alkyl which is optionally mono- or polysubstituted by fluorine, (C$_3$–C$_6$)-cycloalkyl, (C$_3$–C$_6$)-cycloalkyl-(C$_1$–C$_4$)-alkanediyl, (C$_5$–C$_{10}$)-aryl, (C$_5$–C$_{10}$)-aryl-(C$_1$–C$_4$)-alkanediyl, H$_2$N, R$^8$OR$^7$, R$^8$—(C$_5$–C$_{10}$)-arylene-R$^7$, R$^8$R$^8$NR$^7$, R$^8$NHC(O)R$^7$, H$_2$N—C(=NH)—, or H$_2$N—C(=NH)—NH—;

R$^4$ is (C$_{10}$–C$_{14}$)-cycloalkyl, (C$_{10}$–C$_{14}$)-cycloalkyl-(C$_1$–C$_6$)-alkanediyl, it being possible for the cycloalkyl radicals to be bi- or tricyclic, and to be substituted 1–3 times by (C$_1$–C$_6$)-alkyl, trifluoromethyl, pentafluoroethyl, phenyl, benzyl, (C$_1$–C$_6$)-alkoxy, phenoxy, benzyloxy, NH$_2$, =O or mono- or di-(C$_1$–C$_6$-alkyl)-amino; or R$^6$OR$^7$, R$^6$CO$_2$R$^7$, R$^6$OC(O)R$^7$, R$^6$NHR$^7$, R$^6$R$^8$NR$^7$, R$^6$NHC(O)OR$^7$, R$^6$S(O)$_n$NHR$^7$, R$^6$OC(O)NHR$^7$, R$^6$C(O)NHR$^7$, R$^6$C(O)R$^7$, R$^6$NHC(O)NHR$^7$, or R$^6$NHC(O)R$^7$;

R$^5$ is H, (C$_1$–C$_6$)-alkyl, (C$_5$–C$_6$)-cycloalkyl, (C$_5$–C$_6$)-cycloalkyl-(C$_1$–C$_6$)-alkanediyl, trifluoromethyl, pentafluoroethyl, phenyl, or benzyl;

R$^6$ is (C$_{10}$–C$_{14}$)-cycloalkyl, (C$_{10}$–C$_{14}$)-cycloalkyl-(C$_1$–C$_6$)-alkanediyl, it being possible for the cycloalkyl radicals to be bi- or tricyclic, and to be substituted 1–3 times by (C$_1$–C$_6$)-alkyl, trifluoromethyl, pentafluoroethyl, phenyl, benzyl, (C$_1$–C$_6$)-alkoxy, phenoxy, benzyloxy, NH$_2$, =O or mono- or di-(C$_1$–C$_6$-alkyl)-amino;

R$^7$ is a direct bond or (C$_1$–C$_6$)-alkanediyl;

R$^8$ is H, (C$_1$–C$_6$)-alkyl, (C$_3$–C$_6$)-cycloalkyl, (C$_3$–C$_6$)-cycloalkyl-(C$_1$–C$_4$)-alkanediyl, (C$_5$–C$_{10}$)-aryl, or (C$_5$–C$_{10}$)-aryl-(C$_1$–C$_4$)-alkanediyl, it being possible for the alkyl radicals to be substituted by 1–6 fluorine atoms;

R$^9$ is C(O)R$^{10}$;

R$^{10}$ is OH, (C$_1$–C$_6$)-alkoxy, (C$_5$–C$_{10}$)-aryl-(C$_1$–C$_6$)-alkanediyloxy, (C$_5$–C$_{10}$)-aryloxy, (C$_1$–C$_6$)-alkylcarbonyloxy-(C$_1$–C$_4$)-alkanediyloxy, (C$_5$–C$_{10}$)-aryl-(C$_1$–C$_4$)-alkanediylcarbonyloxy-(C$_1$–C$_4$)-alkanediyloxy, NH$_2$, or mono- or di-(C$_1$–C$_6$)-alkyl)-amino;

R$^{11}$ is H, (C$_1$–C$_6$)-alkyl which is optionally mono- or polysubstituted by fluorine, (C$_3$–C$_6$)-cycloalkyl, ($C_3$–$C_6$)-cycloalkyl-($C_1$–$C_4$)-alkanediyl, ($C_5$–$C_{10}$)-aryl, ($C_5$–$C_{10}$)-aryl-($C_1$–$C_4$)-alkanediyl, $H_2N$, $R^8OR^7$, $R^8OC(O)R^7$, $R^8$—($C_5$–$C_{10}$)-arylene-$R^7$, $R^8R^8NR^7$, $R^8NHC(O)R^7$, $R^8C(O)NHR^7$, $H_2N$—C(=NH)—, $H_2N$—C(=NH)—NH—, or =O;

n is 1 or 2;

q is 0 or 1;

in all their stereoisomeric forms and mixtures thereof in any ratio;

and their physiologically tolerable salts.

2. A compound of the formula (I) as claimed in claim 1, in which:

A is a direct bond, ($C_1$–$C_4$)-alkanediyl, —$NR^2$—C(O)—$NR^2$—, —$NR^2$—C(O)O—, —$NR^2$—S(O)$_n$—, —$NR^2$—S(O)$_n$—$NR^2$—, —$NR^2$—CO— or —$NR^2$—, which in each case can be mono- or disubstituted by ($C_1$–$C_4$)-alkanediyl;

B is a direct bond or ($C_1$–$C_6$)-alkanediyl;

D is a direct bond, ($C_1$–$C_4$)-alkanediyl, —O—, —$NR^2$—, —$NR^2$—CO—, —C(O)—$NR^2$—, —$NR^2$—C(O)—$NR^2$—, —$NR^2$—S(O)$_2$—, or —$NR^2$—S(O)—, which in each case can be mono- or disubstituted by ($C_1$–$C_4$)-alkanediyl;

E is phenylene or pyridinediyl which is optionally substituted by 1 or 2 radicals selected from the group consisting of $R^2$ and $R^3$;

F is a direct bond, ($C_1$–$C_6$)-alkanediyl, or —O—, —CO—$NR^2$—, —$NR^2$—CO—, —$NR^2$—C(O)—$NR^2$—, —S(O)$_2$—$NR^2$—, —$NR^2$—S(O)$_2$—, —$CR^2$=$CR^3$—, or —C≡C—, which in each case can be mono- or disubstituted by ($C_1$–$C_4$)-alkanediyl;

G is

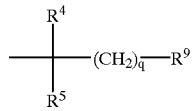

Y is a direct bond or —NH—;

$R^1$ is [$R^2R^3N$—C(=$NR^2$)—,

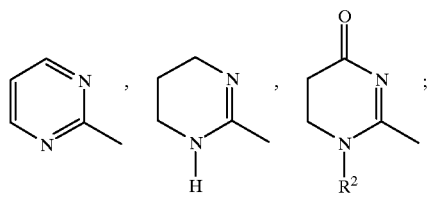

$R^2$, $R^3$ independently of one another are H, ($C_1$–$C_6$)-alkyl, trifluoromethyl, pentafluoroethyl, ($C_5$–$C_6$)-cycloalkyl, ($C_5$–$C_6$)-cycloalkyl-($C_1$–$C_2$)-alkanediyl, phenyl, benzyl, $H_2N$, $R^8OR^7$, $R^8R^8NR^7$, $R^8NHC(O)R^7$, $H_2N$—C(=NH)—, or $H_2N$—C(=NH)—NH—;

$R^4$ is ($C_{10}$–$C_{12}$)-cycloalkyl, ($C_{10}$–$C_{12}$)-cycloalkyl-($C_1$–$C_6$)-alkanediyl, $R^6OR^7$, $R^6R^8NR^7$, $R^6NHC(O)OR^7$, $R^6S(O)_nNHR^7$, $R^6OC(O)NHR^7$, or $R^6C(O)NHR^7$, it being possible for the cycloalkyl radicals to be unsubstituted or substituted 1 or 2 times by ($C_1$–$C_4$)-alkyl, trifluoromethyl, phenyl, benzyl, ($C_1$–$C_4$)-alkoxy, phenoxy, benzyloxy, =O or mono- or di-($C_1$–$C_4$)-alkyl-amino;

$R^5$ is H, ($C_1$–$C_4$)-alkyl, or trifluoromethyl;

$R^6$ is ($C_{10}$–$C_{12}$)-cycloalkyl, or ($C_{10}$–$C_{12}$)-cycloalkyl-($C_1$–$C_6$)-alkanediyl, it being possible for the cycloalkyl radicals to be unsubstituted or substituted 1 or 2 times by ($C_1$–$C_4$)-alkyl, trifluoromethyl, phenyl, benzyl, ($C_1$–$C_4$)-alkoxy, phenoxy, benzyloxy, =O or mono- or di-($C_1$–$C_4$)-akyl)-amino;

$R^7$ is a direct bond or ($C_1$–$C_6$)-alkanediyl;

$R^8$ is H, ($C_1$–$C_6$)-alkyl, ($C_5$–$C_6$)-cycloalkyl, ($C_5$–$C_6$)-cycloalkyl-($C_1$–$C_2$)-alkanediyl, ($C_5$–$C_6$)-aryl, or ($C_5$–$C_6$)-aryl-($C_1$–$C_2$)-alkanediyl;

$R^9$ is C(O)$R^{10}$;

$R^{10}$ is OH, ($C_1$–$C_6$)-alkoxy, phenoxy, benzyloxy, ($C_1$–$C_4$)-alkylcarbonyloxy-($C_1$–$C_4$)-alkanediyloxy, $NH_2$, or mono- or di-($C_1$–$C_6$)-alkyl)-amino;

n is 1 or 2;

q is 0 or 1;

in all their stereoisomeric forms and mixtures thereof in any ratio;

and their physiologically tolerable salts.

3. A compound of the formula (I) as claimed in claim in claim 1, in which:

A is —NH—C(O)—;

B is ($C_1$–$C_4$)-alkanediyl;

D is —O—, —$NR^2$—C(O)—, —C(O)—$NR^2$— or a direct bond;

E is phenylene or pyridinediyl;

F is —$CH_2$— or —C(O)$NHCH_2$—;

G is

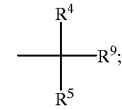

Y is a direct bond;

R is

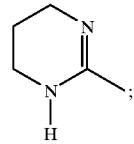

$R^2$ is H or ($C_1$–$C_4$)-alkyl;

$R^4$ is $R^6OC(O)NH$—;

$R^5$ is H;

R is adamantyl-1-($C_1$–$C_3$)-alkylene, adamantyl-2-($C_1$–$C_3$)-alkylene, 1-adamantyl, or 2-adamantyl, wherein said adamantyl is optionally substituted 1 or 2 times by ($C_1$–$C_4$)-alkyl, trifluoromethyl, phenyl, benzyl, ($C_1$–$C_4$)-alkoxy, phenoxy or benzyloxy, or ($C_{11}$–$C_{12}$)-cycloalkyl, which can optionally be substituted 1 or 2 times by ($C_1$–$C_4$)-alkyl, trifluoromethyl, phenyl, benzyl, ($C_1$–$C_4$)-alkoxy, phenoxy or benzyloxy;

$R^9$ is C(O)$R^{10}$, $R^{10}$ is OH, ($C_1$–$C_6$)-alkoxy, phenoxy, benzyloxy or ($C_1$–$C_4$)-alkylcarbonyloxy-($C_1$–$C_4$)-alkanediyloxy;

in all their stereoisomeric forms and mixtures thereof in any ratio; and their physiologically tolerable salts.

4. A compound of the formula (I) as claimed in claim 3, in which A is —($C_1$–$C_8$)-alkanediyl-CO—$NR^2$—($C_1$–$C_8$)-alkanediyl, —($C_1$–$C_8$)-alkanediyl-CO—$NR^2$— or —CO—$NR^2$—($C_1$–$C_8$)-alkanediyl.

5. A compound of the formula (I) as claimed in claim 1, which is selected from the group consisting of:

(a) (2S)-2-(1-adamantylmethyloxycarbonylamino)-3-(4-(2-(1,4,5,6-tetrahydropyrimidin-2-ylcarbamoyl)ethyl)benzoylamino)propionic acid;

(b) (2S)-2-(1-adamantylmethyloxycarbonylamino)-3-(4-(3-(1,4,5,6-tetrahydropyrimidin-2-ylcarbamoyl)propoxyl)phenyl)propionic acid; and their physiologically tolerable salts.

6. A compound of the formula (I) as claimed in claim 2, in which a $(C_{10}-C_{12})$-cycloalkyl radical present in $R^4$ or $R^6$ is 1-adamantyl, 2-adamantyl or $(C_{11}-C_{12})$-cycloalkyl, and a $(C_{10}-C_{12})$-Cycloalkyl-$(C_1-C_5)$-alkanediyl radical present in $R^4$ or $R^6$ is adamantyl-1-$(C_1-C_3)$-alkanediyl or adamantyl-2-$(C_1-C_5)$-alkanediyl, it being possible for each 1-adamantyl, 2-adamantyl and $(C_{11}-C12)$-cycloalkyl radical to be unsubstituted or substituted 1 or 2 times by $(C_1-C_4)$-alkyl, trifluoromethyl, phenyl, benzyl, $(C_1-C_4)$-alkoxy, phenoxy, benzyloxy, =O or mono- or di-$(C_1-C_4$-alkyl)-amino.

7. A pharmaceutical preparation comprising at least one compound of the formula (I) as claimed in claim 3 and/or a physiologically tolerable salts thereof and a suitable excipient.

8. A process for the preparation of a compound of the formula (I) as claimed in claim 1,

in which F is —C(O)NR²— and $R^1$, $R^2$, Y, A, B, D, E, and G are defined as in claim 3, which comprises carrying out a fragment condensation with a compound of the formula (II)

where M is hydroxycarbonyl, $(C_1-C_6)$-alkoxycarbonyl, or activated carboxylic acid derivatives; $R^1$, Y, A, B, D, and E are as defined in claim 3; and HNR²—G, in which $R^2$ and G are as defined in claim 1.

9. A method for inhibiting an interaction between vitronectin receptors and vitronectin receptor ligands in cell-cell or cell-matrix interaction processes, comprising administering a therapeutically effective amount of a compound of formula (I) as claimed in claim 1 and/or a physiologically tolerable salt thereof to a human or animal in need thereof.

10. A method for inhibiting bone resorption by osteoclasts, comprising administering a therapeutically effective amount of a compound of formula (I) as claimed in claim 1 and/or a physiologically tolerable salt thereof to a human or animal in need thereof.

11. A method for inhibiting tumor growth and tumor metastasis, comprising administering a therapeutically effective amount of a compound of formula (I) as claimed in claim 1 and/or a physiologically tolerable salt thereof to a human or animal in need thereof.

12. A method for reducing inflammation, comprising administering a therapeutically effective amount of a compound of formula (I) as claimed in claim 1 and/or a physiologically tolerable salt thereof to a human or animal in need thereof.

13. A method for treating cardiovascular disorders, comprising administering a therapeutically effective amount of a compound of formula (I) as claimed in claim 1 and/or a physiologically tolerable salt thereof to a human or animal in need thereof.

14. A method for treating nephropathies and retinopathies, comprising administering a therapeutically effective amount of a compound of formula (I) as claimed in claim 1 and/or a physiologically tolerable salt thereof to a human or animal in need thereof.

* * * * *

UNITED STATES PATENT AND TRADEMARK OFFICE
CERTIFICATE OF CORRECTION

PATENT NO.     : 6,399,620 B1
DATED          : June 4, 2002
INVENTOR(S)    : Volkmar Wehner et al.

It is certified that error appears in the above-identified patent and that said Letters Patent is hereby corrected as shown below:

<u>Title page,</u>
Item [73], Assignee, please change "Aventis Pharma S.A., Frankfurt (DE)" to
-- Hoechst Aktiengesellchaft, Frankfurt am Main, (DE) and Genentech, Inc., South San Francisco, California --

Signed and Sealed this

Twenty-fourth Day of June, 2003

JAMES E. ROGAN
*Director of the United States Patent and Trademark Office*